US011278721B2

(12) United States Patent
Grill et al.

(10) Patent No.: US 11,278,721 B2
(45) Date of Patent: Mar. 22, 2022

(54) STATE-DEPENDENT PUDENDAL NERVE STIMULATION FOR BLADDER CONTROL

(71) Applicant: Duke University, Durham, NC (US)

(72) Inventors: Warren M. Grill, Chapel Hill, NC (US); James A. Hokanson, Morrisville, NC (US); Christopher L. Langdale, Apex, NC (US)

(73) Assignee: DUKE UNIVERSITY, Durham, NC (US)

( * ) Notice: Subject to any disclaimer, the term of this patent is extended or adjusted under 35 U.S.C. 154(b) by 67 days.

(21) Appl. No.: 16/633,463

(22) PCT Filed: Jul. 23, 2018

(86) PCT No.: PCT/US2018/043255
§ 371 (c)(1),
(2) Date: Jan. 23, 2020

(87) PCT Pub. No.: WO2019/023115
PCT Pub. Date: Jan. 31, 2019

(65) Prior Publication Data
US 2020/0188661 A1    Jun. 18, 2020

Related U.S. Application Data

(60) Provisional application No. 62/688,693, filed on Jun. 22, 2018, provisional application No. 62/536,010, filed on Jul. 24, 2017.

(51) Int. Cl.
*A61N 1/36*        (2006.01)

(52) U.S. Cl.
CPC ..... *A61N 1/36007* (2013.01); *A61N 1/36171* (2013.01); *A61N 1/36178* (2013.01)

(58) Field of Classification Search
CPC ........... A61N 1/36007; A61N 1/36171; A61N 1/36178; A61N 1/36164
See application file for complete search history.

(56) References Cited

U.S. PATENT DOCUMENTS

| 6,907,293 B2* | 6/2005 | Grill | A61N 1/0556 607/2 |
| 2006/0122660 A1* | 6/2006 | Boveja | A61N 1/3605 607/40 |
| 2009/0326603 A1* | 12/2009 | Boggs, II | A61N 1/36196 607/41 |

(Continued)

FOREIGN PATENT DOCUMENTS

| WO | 2017/021909 | 2/2017 | |
| WO | WO-2017021909 A1 * | 2/2017 | A61N 1/05 |

(Continued)

OTHER PUBLICATIONS

International Search Report and Written Opinion of the International Searching Authority, dated Nov. 6, 2018 in corresponding International Patent Application No. PCT/US2018/043255.

*Primary Examiner* — Catherine M Voorhees
(74) *Attorney, Agent, or Firm* — Wenderoth, Lind & Ponack, L.L.P.

(57) ABSTRACT

The present disclosure provides a device for state-dependent pudendal nerve stimulation for bladder control in a subject and methods of making and using the same.

26 Claims, 16 Drawing Sheets

(56) References Cited

U.S. PATENT DOCUMENTS

2011/0276055 A1* 11/2011 Possover ............ A61N 1/36107
606/129
2016/0263376 A1* 9/2016 Yoo .................... A61N 1/36017

FOREIGN PATENT DOCUMENTS

WO        2017/066572        4/2017
WO    WO-2017066572 A1 *    4/2017    .............. A61P 13/10

* cited by examiner

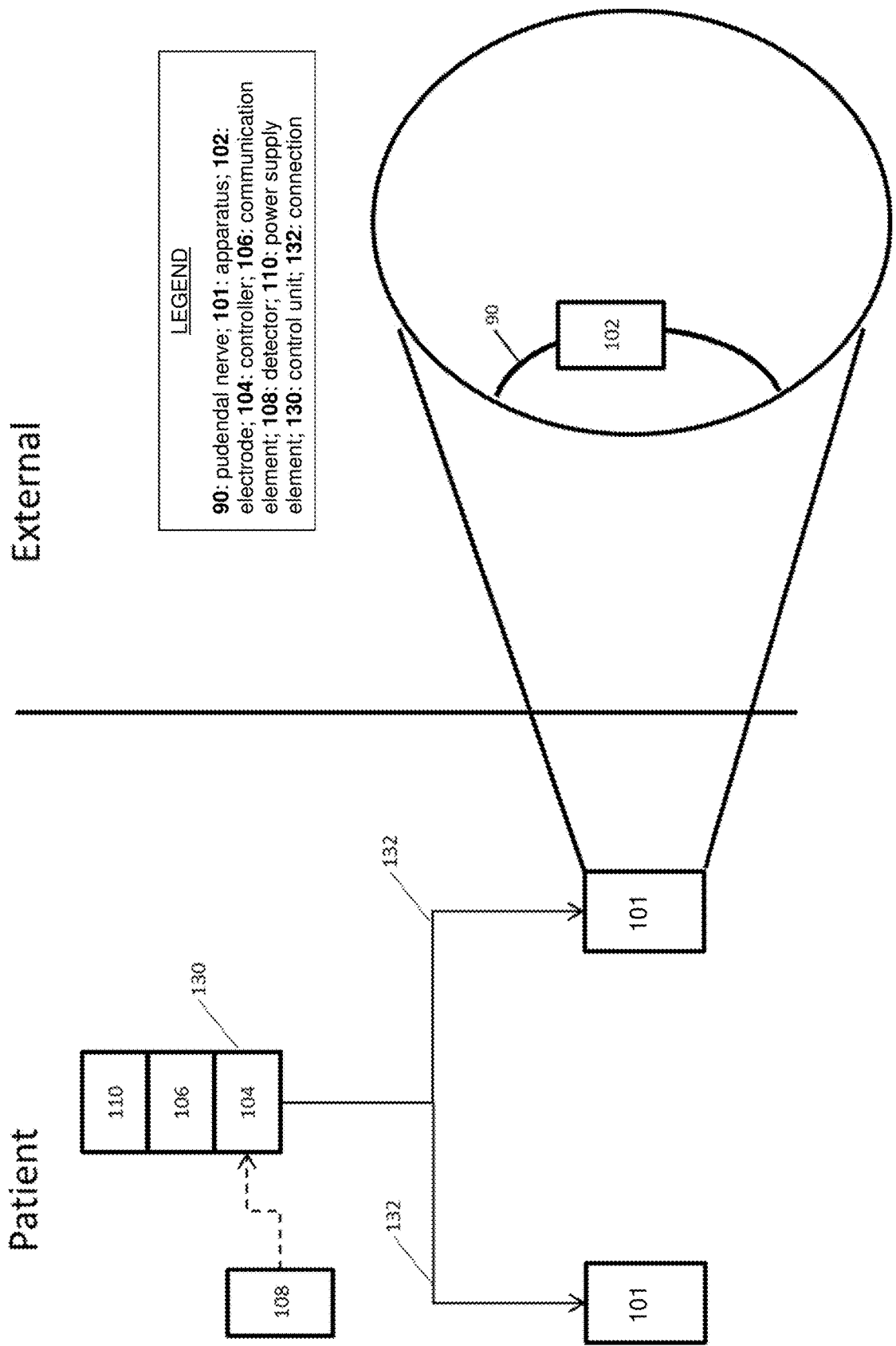

Figure 12
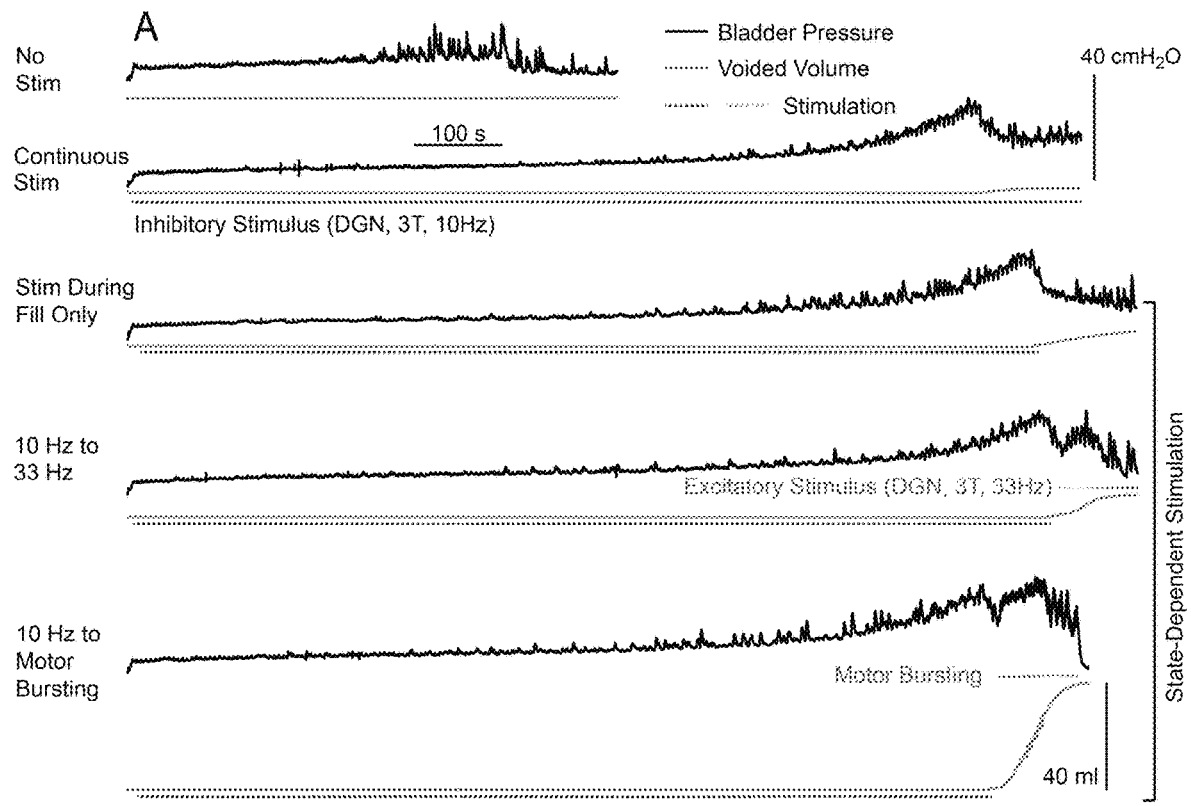
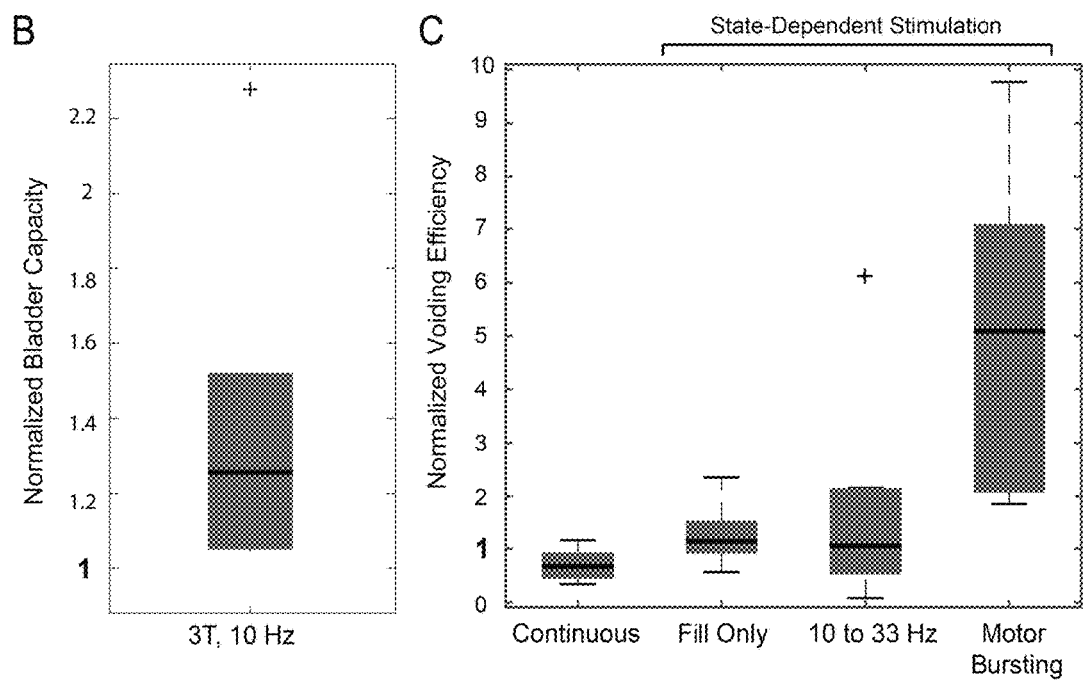

Figure 14
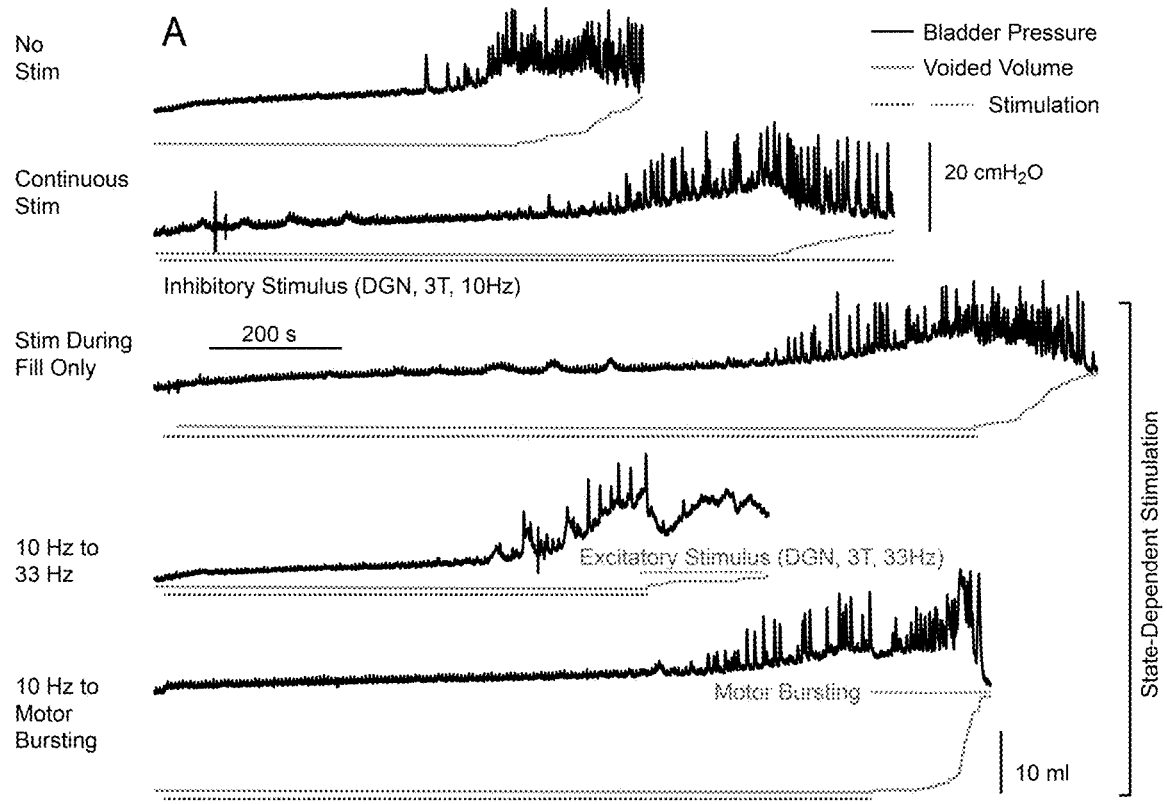
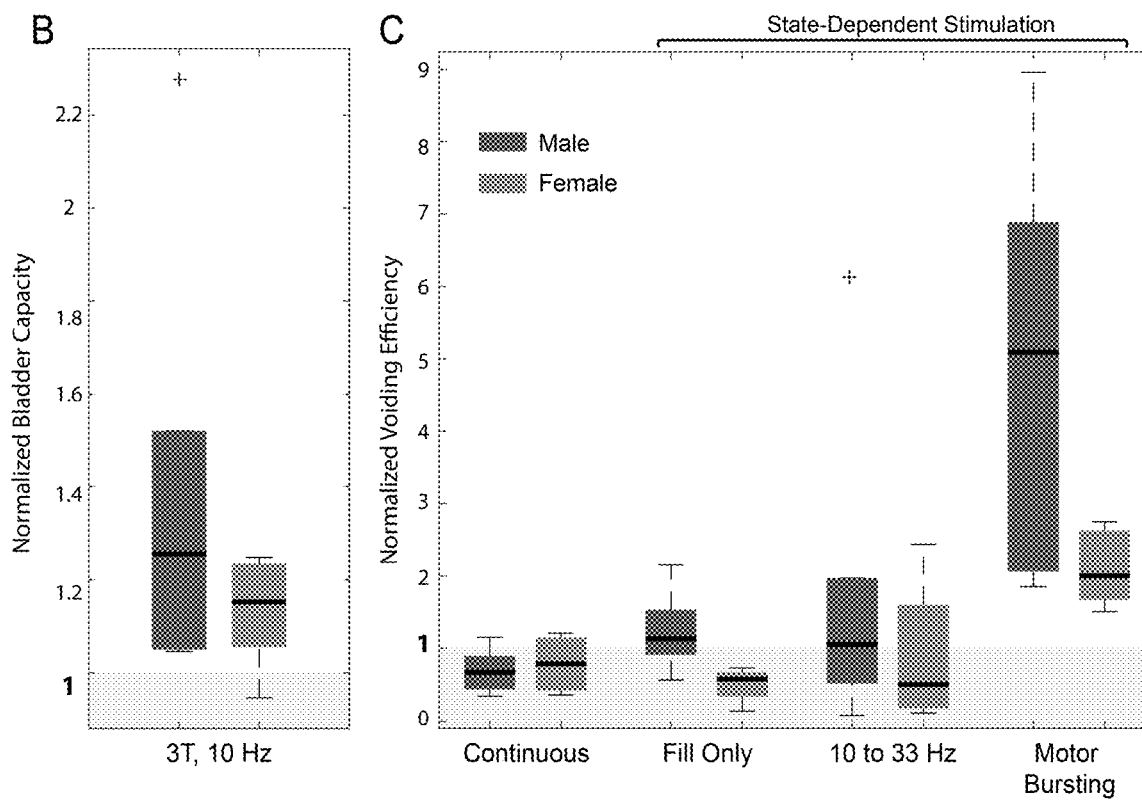

STATE-DEPENDENT PUDENDAL NERVE STIMULATION FOR BLADDER CONTROL

Bladder function is comprised of two phases: a filling phase (urine storage) and a voiding phase (urine evacuation) and efficient bladder function involves control of these phases mediated by continence and micturition reflexes accomplished through coordinated sympathetic, parasympathetic and somatic neural activity [Beckel and Holstege *Neurophysiology of the Lower Urinary Tract*, in *Urinary Tract* (2011) Springer Berlin Heidelberg, 149-169]]. In bladder dysfunction (such as over-active bladder (OAB), underactive bladder (UAB) or urinary retention), one or more of these functions is disrupted, leading to symptoms including urinary urgency, frequency, urgency incontinence, and nocturia. These symptoms often fail to improve following pharmacological treatment (Brindley et al. *Br J Urol* 46: 453-62, 1974).

Alternatives to pharmacological treatment of bladder dysfunction including sacral nerve neuromodulation and posterior tibial nerve stimulation have had only limited success (Mangera et al. & Siddiqui et al.). These approaches can require major surgical intervention or frequent visits with a medical professional, thereby limiting the suitability of such treatments in the majority of patients. Thus, there is a need for therapies for bladder dysfunction.

Pudendal nerve stimulation is a promising therapeutic option for treatment of OAB and bladder dysfunction symptoms, though it remains unclear how to optimally stimulate the pudendal nerve to reduce the symptoms of bladder dysfunction.

WO2017/066572 describes stimulation of the pudendal nerve with a high intensity electrical signal to improve bladder capacity.

SUMMARY OF THE INVENTION

The inventors have investigated electrical stimulation of the pudendal nerve, and the branches thereof, and have devised an apparatus, and methods of using such an apparatus, which addresses the shortcomings of previous treatments for bladder dysfunction. In particular, WO2017/066572 describes high intensity stimulation of the pudendal nerve to increase bladder capacity. The inventors describe that low intensity stimulation of the pudendal nerve improves bladder capacity. This has the advantage that the battery life of any apparatus applying the signal is prolonged, thereby making the apparatus more efficient and providing greater convenience for both the patient and clinicians.

Furthermore, the inventors have identified that the improvement in bladder capacity arising from low intensity stimulation of the pudendal nerve is prolonged—that is, it is carried over from one micturition cycle to the next even in the absence of further stimulation. The surprising finding that low intensity pudendal nerve stimulation improves bladder capacity for at least 1 or 2 micturition cycles after stimulation has stopped means that stimulation does not need to be applied every micturition cycle for treatment to be effective. This further extends the potential battery life of any apparatus applying the stimulation and greatly improves patient comfort.

Bladder function is comprised of two phases: a filling phase (urine storage) and a voiding phase (urine evacuation). It is therefore desirable to improve the function of both phases in a patient experiencing bladder dysfunction. As described in the Examples, as well as improving bladder capacity, pudendal nerve stimulation can improve voiding efficiency. The approaches to improving voiding efficiency described herein are applicable in scenarios in which a low intensity pudendal nerve stimulation has been used to improve bladder capacity, and also when a high intensity pudendal nerve stimulation has been used to improve bladder capacity Examples below demonstrate that electrical stimulation of the pudendal nerve during the bladder filling phase followed by termination of stimulation at onset of voiding phase results in improved voiding efficiency compared to controls in which no stimulation has been applied. The Examples also demonstrated that voiding efficiency can be further improved by application of a second electrical signal during voiding phase. In particular, application of a second electrical signal of higher frequency than the first electrical signal results in improved voiding efficiency. Similarly, application of a second electrical signal to motor fibres of the pudendal nerve in a burst pattern also results in improved voiding efficiency.

Therefore, in a first aspect, the present disclosure provides an apparatus for stimulating neural activity in a pudendal nerve of a subject, the apparatus comprising, consisting of, or consisting essentially of: at least one primary electrode configured to apply a first electrical signal to said nerve; and a controller coupled to said primary electrode(s) and controlling the first electrical signal to be applied thereby, wherein said controller is configured to cause said at least one primary electrode to apply said first electrical signal that stimulates neural activity in the pudendal nerve to produce an increase in bladder capacity, wherein the first electrical signal comprises an AC waveform having a frequency in the range of from 0.1-50 Hz, preferably 1-50 Hz, and wherein the first electrical signal has an amplitude in the range from 0.05 T to 10 T.

In a further aspect, the present disclosure provides a method of treating bladder dysfunction in a subject comprising, consisting of, or consisting essentially of applying a first electrical signal to a pudendal nerve of the subject, wherein the first electrical signal comprises an AC waveform having a frequency in the range of from 1-50 Hz and wherein the first electrical signal has an amplitude in the range of from 0.05 T to 10 T.

In some embodiments, the first signal comprises a "low intensity" signal. In some embodiments, the first electrical signal comprises an amplitude in the range from 0.05 T to <2.0 T. In some embodiments, the first electrical signal comprises an amplitude in the range from 0.3 T to <2.0 T. In some embodiments, the first electrical signal comprises an amplitude in the range of from 1 T to 1.5 T. In other embodiments, the first electrical signal comprises an amplitude of 1 T. In yet other embodiments, the first electrical signal comprises an amplitude of 1.5 T.

In another embodiment, the first electrical signal comprises a frequency in the range of from 1-20 Hz. In some embodiments, the first electrical signal comprises a frequency of 10 Hz. In other embodiments, the first electrical signal comprises a frequency of 20 Hz.

In another embodiment, the first electrical signal is applied no more frequently than alternate micturition cycles. In other embodiments, the first electrical signal is applied no more frequently than every third micturition cycle.

In another embodiment, the first signal comprises a "high intensity" signal. In such embodiments, the first electrical signal comprises an amplitude in the range from 2 T to 10 T. In other embodiments, the first electrical signal comprises an amplitude in the range from 2 T to 4 T. In yet another embodiment, the first electrical signal comprises an amplitude comprising 3 T.

In some embodiments, the first electrical signal comprises an AC waveform having a frequency in the range of from 0.1 to 50 Hz. In some embodiments, the first electrical signal comprises an AC waveform having a frequency in the range of from 1 to 50 Hz. In some embodiments, the first electrical signal applied comprises an AC waveform having a frequency of 1 to 45 Hz. In yet other embodiments, the first electrical signal applied comprises an AC waveform having a frequency in the range of from 2 to 40 Hz. In other embodiments, the first electrical signal comprises a frequency in the range of 1 to 10 Hz. In one embodiment, the first electrical signal comprises a frequency of 10 Hz.

In yet another embodiment comprising either "high intensity" or "low intensity" first electrical signals, the signal is applied to sensory fibres of the pudendal nerve. In some embodiments, the signal is applied to a sensory branch of the pudendal nerve, for example the dorsal nerve of the penis/clitoris (DNP, also known as the dorsal genital nerve). In some embodiments of the apparatus of the invention, the at least one primary electrode is configured to apply the first electrical signal to sensory fibres of said pudendal nerve, and the controller is configured to cause said at least one primary electrode to apply the first electrical signal that stimulates neural activity in sensory fibres of the pudendal nerve to produce an increase in bladder capacity.

In some embodiments, application of the first electronic signal is stopped at onset of a bladder voiding phase. In relation to the apparatus of the invention, in certain embodiments the controller causes the first electronic signal to be stopped when onset of a voiding phase is detected. In certain embodiments, the application of the first signal and no second signal provides a positive voiding effect in a male subject and a negative voiding effect in a female subject.

As noted above, bladder function can be further improved by increasing voiding efficiency through application of a second electrical signal. Therefore, in some embodiments of both "high intensity" and "low intensity" first electrical signal embodiments, a second electrical signal is applied to stimulate the pudendal nerve or branches thereof. In such embodiments, the second electrical signal can be applied by said at least one primary electrode(s). In certain alternative embodiments, the apparatus comprises at least one secondary electrode coupled to the controller and the second electrical signal is applied by the at least one secondary electrode(s), the controller controlling the signal to be applied thereby.

In certain embodiments, the second electronic signal comprises an AC waveform having a higher frequency than the first electronic signal.

In certain embodiments where a second electrical signal is to be applied, the second electrical signal comprises an AC waveform having a frequency in the range of from 20-50 Hz. In certain embodiments, the second electrical signal comprises an AC waveform having a frequency of 30-40 Hz, optionally 33 Hz or 40 Hz. In certain embodiments wherein the second electrical signal has a frequency higher than the first electrical signal, the second electrical signal has a frequency of 33 Hz.

In some embodiments, the controller is configured to cause a second electrical signal to be applied, wherein said second electrical signal stimulates neural activity in the pudendal nerve to produce an increase in voiding efficiency and wherein the second electrical signal comprises an AC waveform having a frequency in the range of from 20 to 50 Hz. In some embodiments, the second electrical signal applied comprises an AC waveform having a frequency of 20 to 45 Hz. In yet other embodiments, the second electrical signal comprises an AC waveform having a frequency in the range of from 20 to about 40 Hz. In some embodiments, the second electrical signal comprises an AC waveform having a frequency of about 33 Hz. In certain embodiments, the application of 33 Hz provides a positive voiding effect in a male subject and a negative voiding effect in a female subject.

In certain embodiments, the second electrical signal comprises an AC waveform and is applied in a burst pattern. In such embodiments of the apparatus of the invention, the apparatus comprises at least one secondary electrode coupled to the controller and the second electrical signal is applied by the at least one secondary electrode(s), wherein the controller is configured to cause the second electrical signal to be applied in a burst pattern.

In certain embodiments, the burst pattern comprises a signal burst having a duration of from 50 ms to 1000 ms. In certain embodiments, the burst pattern comprises a signal burst having a duration of 100 ms.

In such embodiments, the burst pattern comprises of a signal burst having a duration from 50 ms to 1000 ms repeated at an interval of from 0.125 s to 2 s. In certain preferred embodiments, the burst pattern comprises of a signal burst having a duration of 100 ms repeated at an interval of 0.5 s.

In some embodiments the burst pattern consists of a signal burst having a duration from 50 ms to 1000 ms repeated at an interval of from 0.125 s to 2 s. In some embodiments, the burst pattern consists of a signal burst having a duration from 50 ms to 1000 ms repeated at an interval of from 0.2 s to 2 s. In certain preferred embodiments, the burst pattern consists of a signal burst having a duration of 100 ms repeated at an interval of 0.5 seconds.

In certain embodiments wherein the second electrical signal is to be applied in a burst pattern, the second electrical signal is to be applied to motor fibres of the pudendal nerve, for example to a motor branch of the pudendal nerve. In such embodiments of the apparatus of the invention, the at least one secondary electrode(s) is (are) configured to apply the second electrical signal to motor fibres of said pudendal nerve, and the controller is configured to cause said at least one secondary electrode to apply the second electrical signal that stimulates neural activity in motor fibres of the pudendal nerve to produce an increase in voiding efficiency.

In yet other embodiments, the second electrical signal applied in a burst pattern comprises an AC waveform having a frequency in the range of from 20 to 50 Hz. In some embodiments, the second electrical signal applied in a burst pattern comprises an AC waveform having a frequency of 20 to 45 Hz. In one embodiment, the second electrical signal applied in a burst pattern comprises an AC waveform having a frequency of 40 Hz.

The second electrical signal applied in a burst pattern may be at a frequency 40 Hz applied in pulses at different intervals, for example 0.125 seconds, 0.21 seconds and 0.5 seconds.

In yet other embodiments, the second electrical signal applied in a burst pattern comprises an AC waveform repeated at a frequency in the range of from 2 to 20 Hz. In some embodiments, the second electrical signal applied in a burst pattern comprises an AC waveform repeated at a frequency in the range of 2 to 10 Hz. In one embodiment, the second electrical signal comprises an AC waveform repeated at a frequency of 10 Hz. In another embodiment, the second electrical signal is repeated at a frequency of 2 Hz. In another embodiment, the second electric signal is repeated at a frequency of 4.76 Hz. In another embodiment, the second electric signal is repeated at a frequency of 8 Hz.

In some embodiments where a second electrical signal is (to be) applied, the second electrical signal comprises an AC waveform having an amplitude in the range of 0.5-4 T. In some embodiments, the second electrical signal comprises an AC waveform having an amplitude in the range 1-3 T. In some embodiments, the second electrical signal comprises an amplitude of about 3 T. In other embodiments wherein the second electrical signal is applied in a burst pattern, the second electrical signal comprises an amplitude of 1 T. In certain embodiments wherein the second electrical signal has a frequency higher than the first electrical signal, the second electrical signal has an amplitude of 3 T. In certain embodiments wherein the second electrical signal is applied in a burst pattern, the second electrical signal has an amplitude of 1.8-2.3 T.

In a further aspect the invention provides a method of treating bladder dysfunction in a subject comprising: i. implanting in the subject an apparatus according to the first aspect; ii. positioning at least one primary electrode of the apparatus in signalling contact with a pudendal nerve of the subject and, when the apparatus comprises at least one secondary electrode, positioning said at least one secondary electrode of the apparatus in signalling contact with a pudendal nerve of the subject; iii. activating the apparatus to apply an electrical signal to the pudendal nerve of the subject as caused by the controller.

Apparatuses and methods according to the invention have the further advantage that they can be used in conjunction with pharmaceutical therapies for bladder dysfunction to reduce symptoms.

Therefore, in a further aspect the invention provides a pharmaceutical composition comprising a compound for treating bladder dysfunction, for use in a method of treating bladder dysfunction in a subject, wherein the method is a method according to the invention, the method further comprising the step of administering an effective amount of the pharmaceutical composition to the subject.

In a further aspect, the invention provides a pharmaceutical composition comprising a compound for treating bladder dysfunction, for use in treating bladder dysfunction in a subject, the subject having an apparatus according to the invention implanted.

In certain embodiments, the compound for treating bladder dysfunction is an antimuscarinic compound or a β-adrenergic receptor agonist, optionally a β3-adrenergic receptor agonist. In certain embodiments, the antimuscarinic compound is selected from darifenacin, hyoscyamine, oxybutynin, tolterodine, solifenacin, trospium, or fesoterodine. In certain embodiments, the β3-adrenergic receptor agonist is mirabegron.

In a further aspect, the invention provides a neuromodulation system comprising a plurality of apparatuses according to the invention. In certain embodiments, each apparatus is arranged to communicate with at least one other apparatus in the system, optionally all apparatuses in the system. In certain embodiments, the system further comprises a processor arranged to communicate with the apparatuses of the system.

In a preferred embodiment of all aspects of the invention, the subject to be treated or for which the apparatus is to be used is a human subject.

In certain embodiments the subject is a male subject. In certain embodiments the subject is a female subject.

In all aspects, unless specified otherwise, "pudendal nerve" refers to the pudendal nerve and its branches. In certain embodiments, the first and/or second electronic signal is (to be) applied to the motor branch of the pudendal nerve. In certain embodiments, the first and/or second electronic signal is (to be) applied to the sensory branch of the pudendal nerve, In certain embodiments, the first and/or second electronic signal is (to be) applied to dorsal nerve of the penis/clitoris (DNP). In certain embodiments, the first and/or second electronic signal is (to be) applied to perineal nerve.

Another aspect of the present disclosure provides all that is disclosed and illustrated herein.

(A) Bladder capacity values for each trial in an experiment. Circles indicate the start of each trial. Black rectangles have been added to highlight trials which show a stimulus carryover effect. (B) Sequential trials collected during a single experiment. Stimulation at 0.6 T, 20 Hz (trial 0) increased bladder capacity and initially disrupted coordinated voiding. On the subsequent trial (trial 1) the bladder capacity remained increased. On the subsequent and final trial of the series and the experiment (trial 2) the bladder capacity decreased, but remained elevated compared to the control trial (trial−1) conducted prior to stimulation. (C) Distributions of scaled bladder capacity on the three trials following stimulation at 1 or 1.5 T and 10 or 20 Hz. Bladder capacities were scaled such that 0% is the bladder capacity of the trial preceding stimulation and 100% is the bladder capacity of the stimulation trial. Only groups of trials in which stimulation increased bladder capacity by at least 20% relative to the preceding trial and in which at least three non-stimulation trials followed are included (n=15, 48% of trials). Box plots were created using Matlab's boxplot( ) command and the centre bars represent the median value, box edges are the 25th and 75th percentiles, and the whiskers extend to the most extreme data points which are not considered to be outliers.

Figure 6:
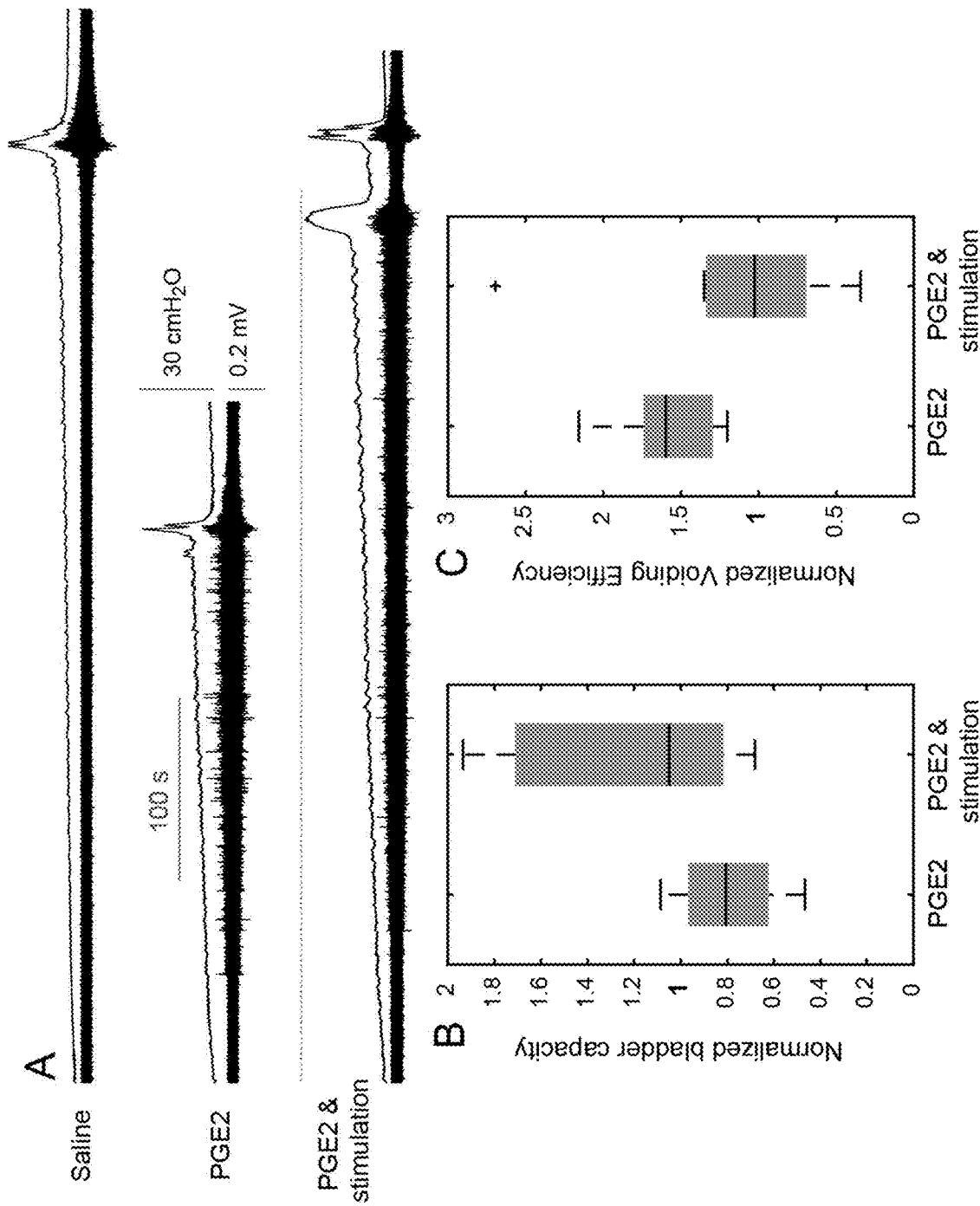

FIG. 6: Sensory pudendal nerve stimulation increases bladder capacity in an intravesical PGE2 model of overactive bladder.

(A) Example traces showing a decrease in bladder capacity with intravesical PGE2 and increase in bladder capacity with sensory pudendal stimulation. (B) Bladder capacity decreased with PGE2 (p=0.02) and increased (relative to PGE2) with stimulation (p=0.004) (n=9). (C) Voiding efficiency increased with PGE2 (p<0.001) and decreased (relative to PGE2) with stimulation (p=0.05; p=0.01 with removal of the outlier). All stimulation was at 20 Hz with amplitudes ranging from 100 to 800 μA (mean 330±63 μA S.E.). Voided volume (to compute the voiding efficiency) consists of volume expelled during the first micturition event through one minute following stimulus termination.

Figure 7:
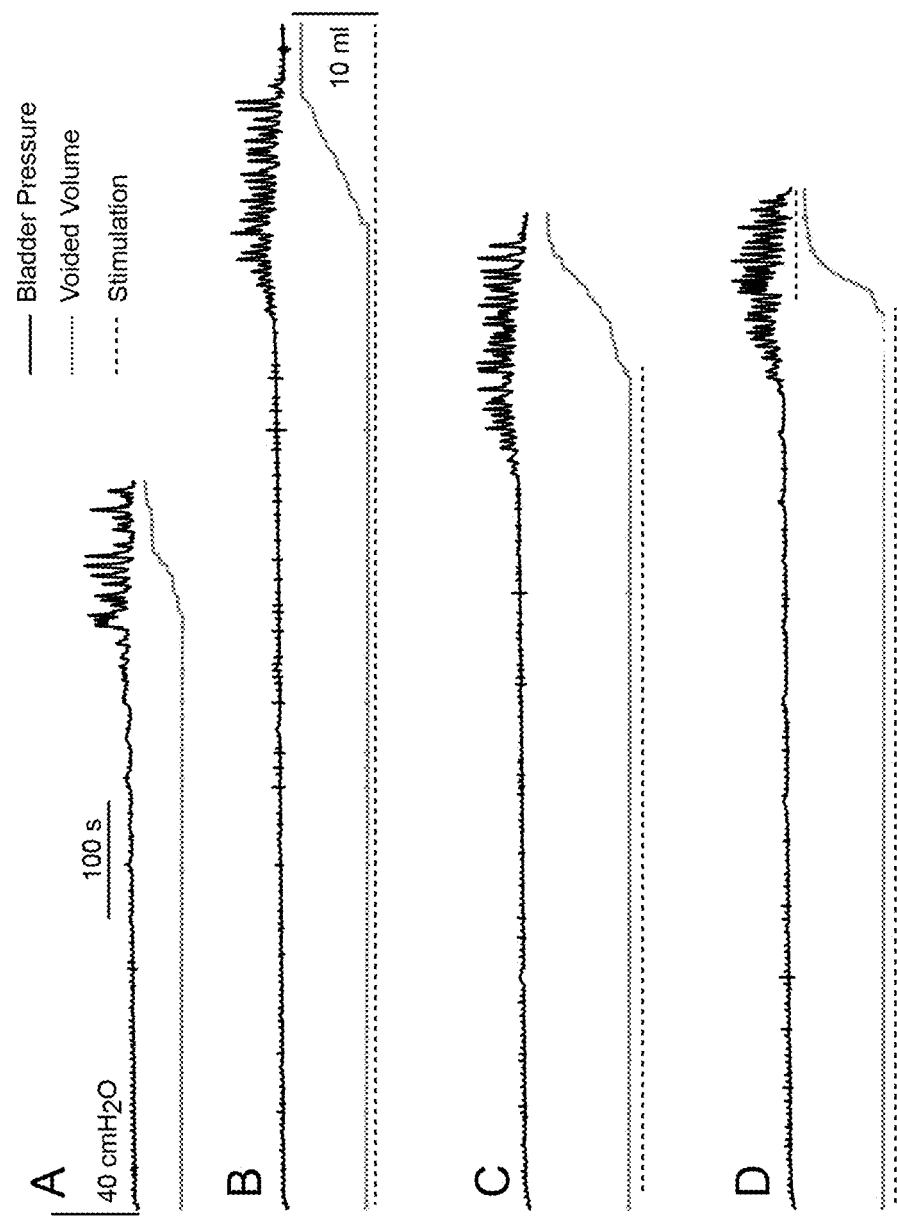

FIG. 7: Increases in bladder capacity and voiding efficiency from state-dependent stimulation—Experiment 1

(A) Example trial in which no stimulation occurred. Average bladder capacity and voiding efficiency from this type of trial were 12.5 ml and 28% respectively. (B) Stimulation at 3 T, 10 Hz (DNP) increased bladder capacity and voiding efficiency (17.9 ml, 36%—averages). These stimulation parameters were also used for (C) and (D), but with different stimulus parameters during the void (state-dependent stimulation). (C) Stimulus was terminated at void onset, further increasing voiding efficiency (16.8 ml, 46%—averages). (D) Stimulation at 3 T, 33 Hz (DNP) during voiding which also had a higher voiding efficiency than stimulation throughout (18.2 ml, 46%).

Figure 8:
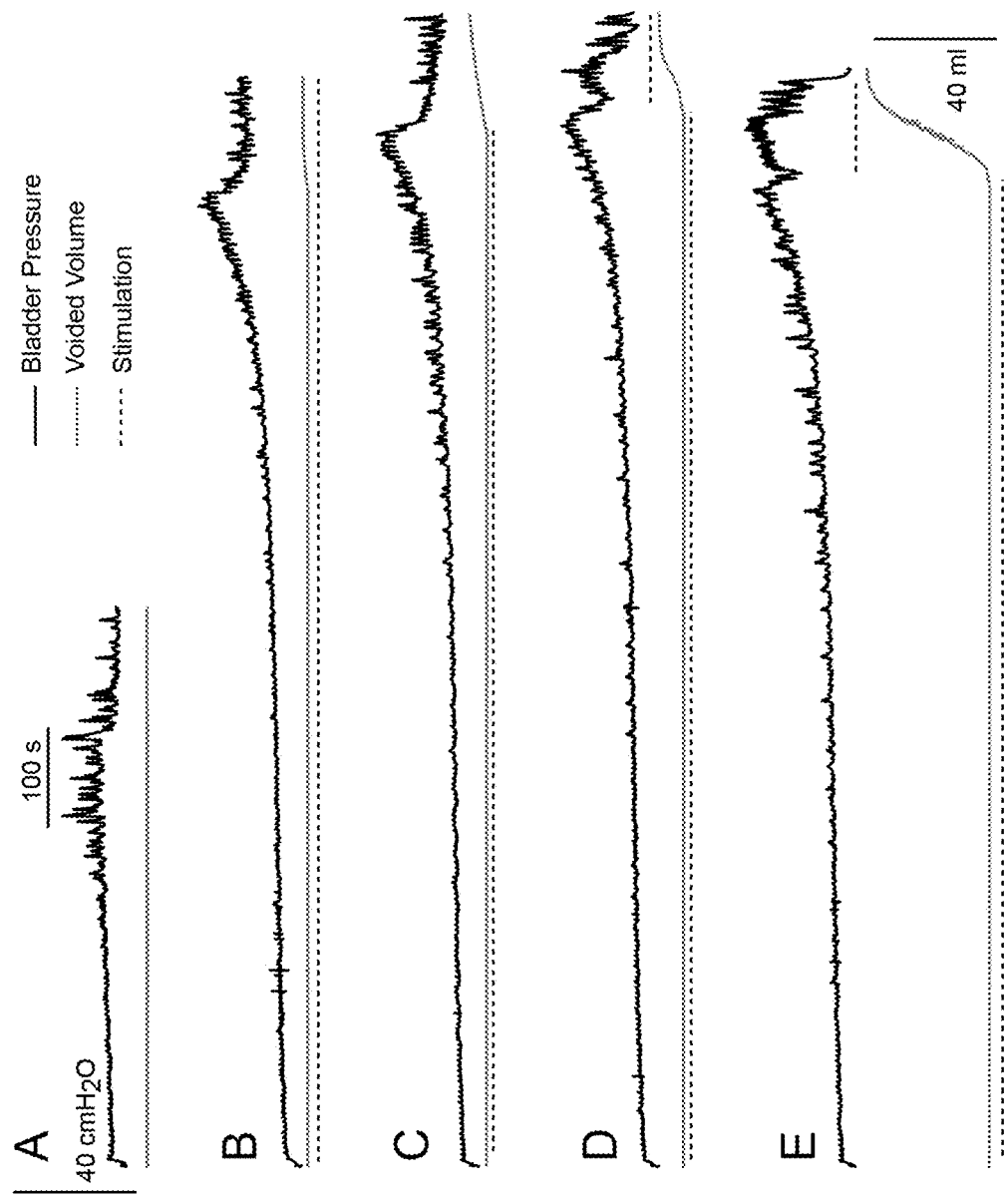

FIG. 8: Increases in bladder capacity and voiding efficiency from state-dependent stimulation—Experiment 2

(A) Example trial without stimulation. Average bladder capacity and voiding efficiency values from all such trials was 17.2 ml and 6%. (B) Stimulation throughout a trial at 3 T, 10 Hz (DNP) increased bladder capacity but not voiding efficiency (43.3 ml, 4%,—averages). (C) Same as B, but with termination of the stimulus at void onset. These trials had increased voiding efficiency relative to stimulation throughout (43.9 ml, 17%—averages). (D) Same as B, but with 3 T, 33 Hz stimulation (DNP) during voiding. These trials also had increased voiding efficiency (47.6 ml, 19%—averages). (E) Same as B, but with burst stimulation of pudendal motor nerve during voiding, which led to increased voiding efficiency (50.8 ml, 83%—averages).

Figure 9:
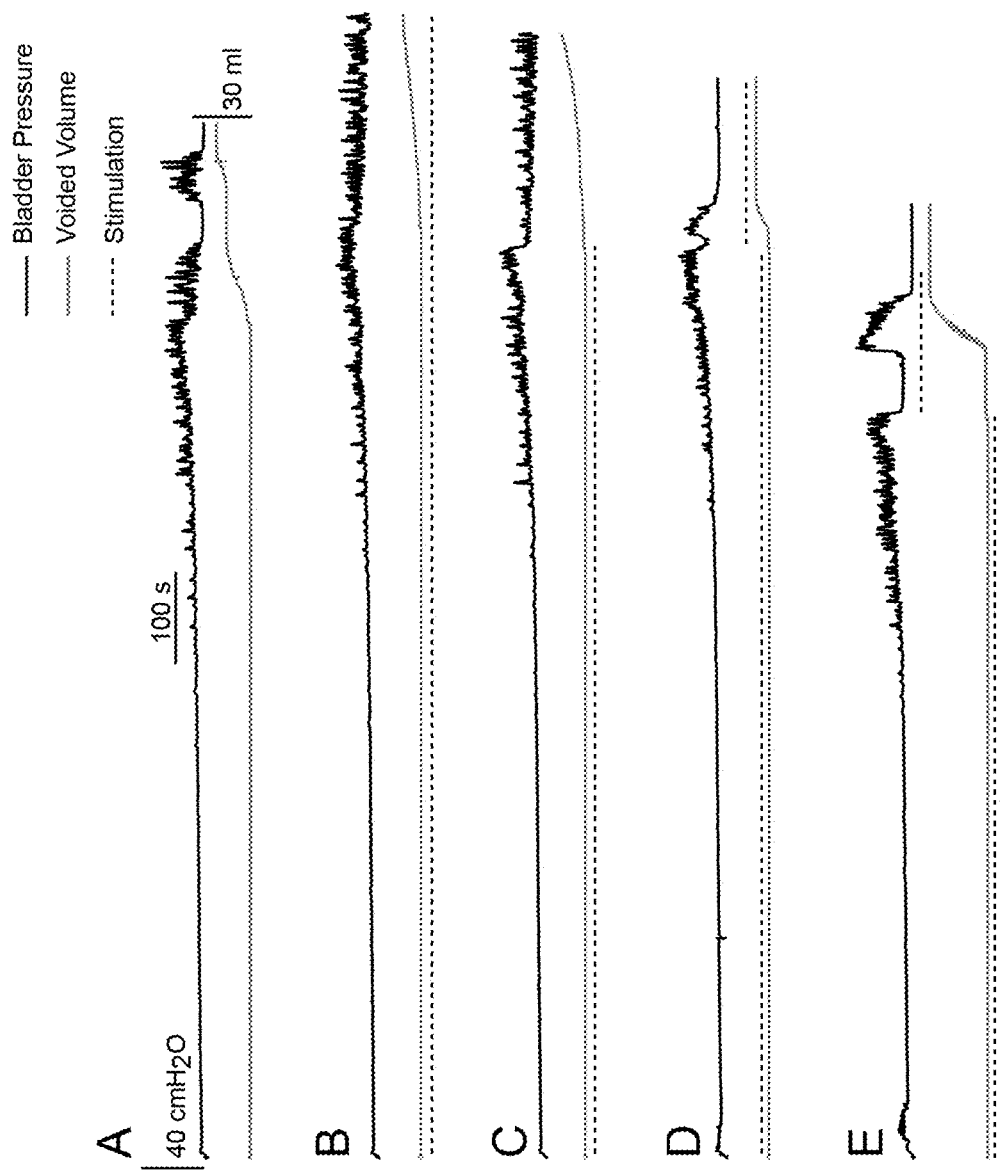

FIG. 9: Increases in bladder capacity and voiding efficiency from state-dependent stimulation—Experiment 3

(A) Example trial without stimulation. Average bladder capacity and voiding efficiency values were 37.2 ml and 41%. (B) Stimulation throughout (3 T, 10 Hz, DNP) increased bladder capacity slightly (40.8 ml) with a decrease in voiding efficiency (20%). (C) Termination of the stimulus at void onset did not improve voiding efficiency (39.9 ml, 22%—averages), nor did switching to stimulation at 33 Hz (D) (38.3 ml, 14%—averages). (E) Motor burst stimulation increased voiding efficiency (40.8 ml, 78%—averages).

Figure 10:
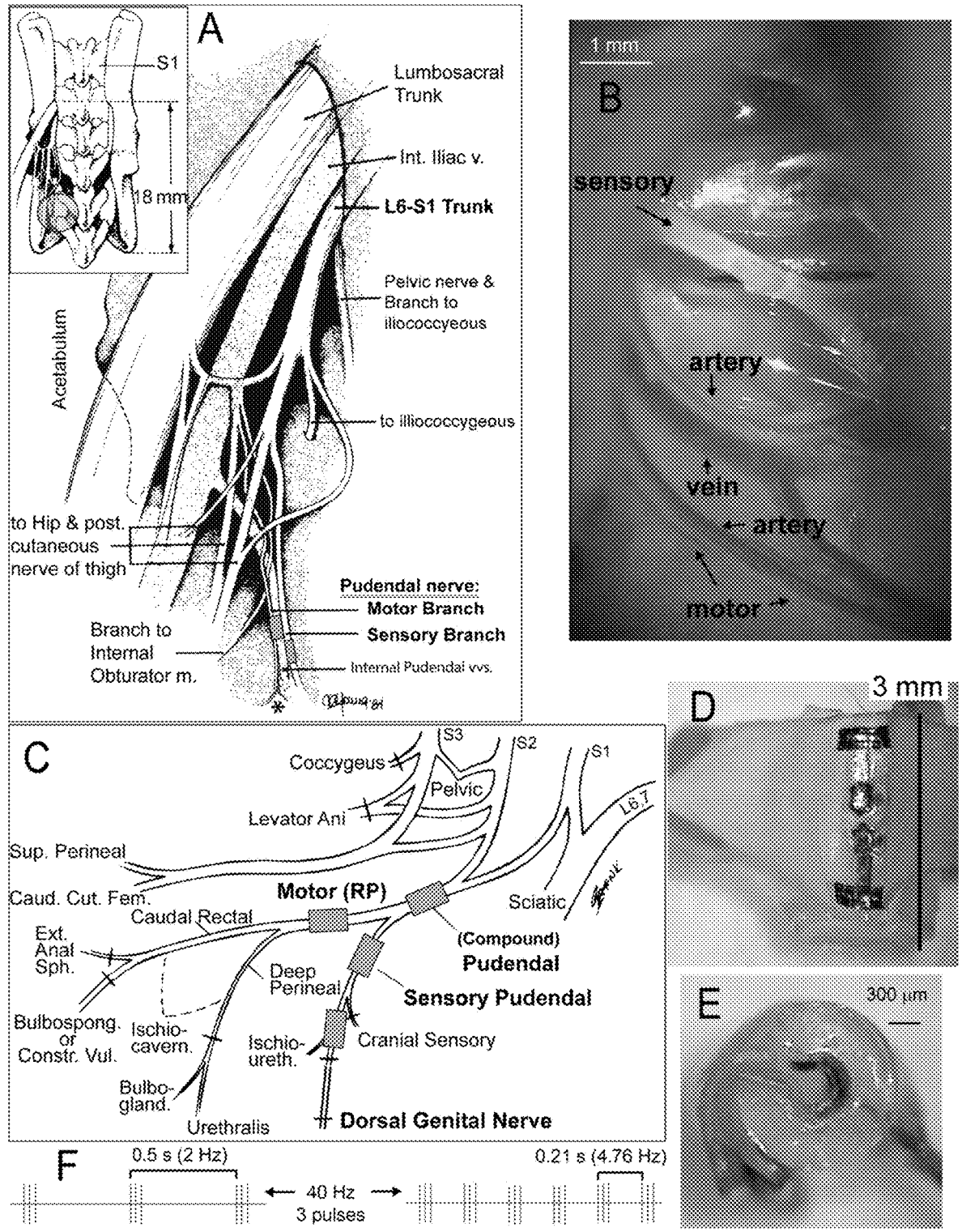

FIG. 10: Experimental setup and lower urinary tract anatomy.

A) Neuroanatomy of the rat lower urinary tract, including the sacral plexus and pudendal nerve (modified from McKenna and Nadelhaft, 1986). The inset shows this neuroanatomy relative to the pelvic bones and spinal column. The highlighted circle (in inset) shows our surgical access point in the ischiorectal fossa. Grey boxes indicate placement of nerve cuffs on the sensory branch as well as on the motor branch. B) Photo of the isolated sensory branch. A CorTec cuff has been placed next to, but not on the nerve (modified from Hokanson et al., 2017a). C) Neuroanatomy of the male cat lower urinary tract (modified from Martin et al., 1974). Dorsal genital nerve cuff was placed proximal to splitting of ischiourethralis branch. In females a nerve cuff was placed proximal to the splitting of the cranial sensory branch. D) A nerve cuff (CorTec) in the open position with stimulation sites exposed. The only point of exposure of the two stimulation sites for this model are at the edges of the cuff, the rest of the metal is insulated. E) Side view of the same nerve cuff in the closed position showing the 300 μm diameter opening. F) Two of the three "bursting" stimulation patterns employed for this study. Each tick represents a biphasic stimulation pulse. In all trials (rat and cat) the burst consisted of 3 pulses at 40 Hz. The time between bursts varied depending on trial type and consisted of 0.125 (8 Hz, rat), 0.21 (4.76, rat), or 0.5 s (2 Hz, rat and cat) between burst starts.

Figure 11:
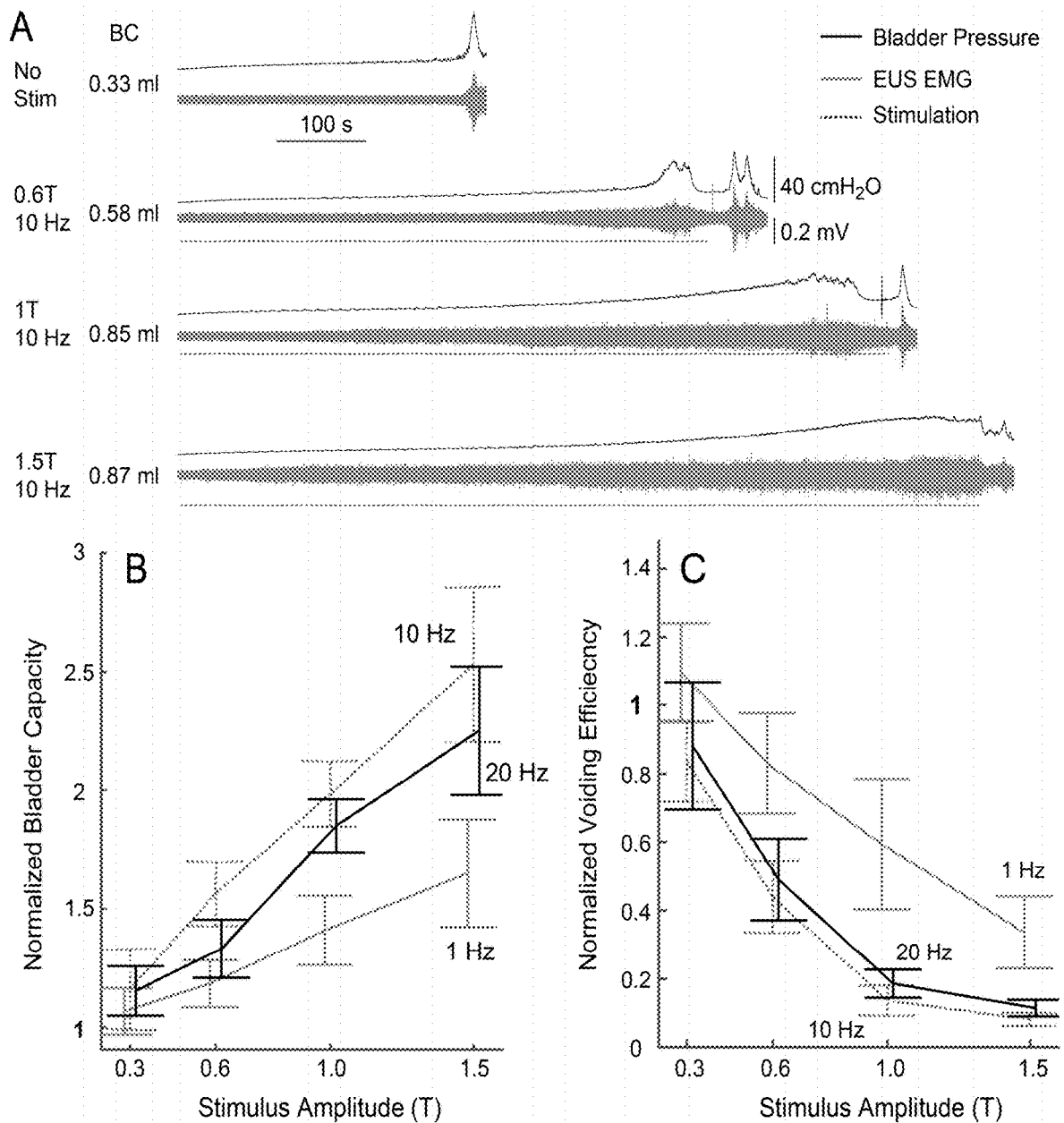

FIG. 11: Continuous stimulation of the sensory pudendal nerve in the female rat increased bladder capacity but decreased voiding efficiency.

A) Example cystometrograms from a single rat. Increasing stimulation amplitude increased bladder capacity as evident by the increase in fill time. The magnitude of bladder contraction decreased with increasing amplitude, which resulted in decreased voiding efficiency. Stimulation continued through the first contraction/leak event. A second contraction was also recorded without stimulation, but these second contractions were insufficient to increase voiding efficiency back to baseline. B) Summary bladder capacity data at 1, 10, and 20 Hz. Increasing stimulation amplitude increased bladder capacity, with the largest increases at 10 Hz. C) Summary voiding efficiency data at 1, 10, and 20 Hz. Increasing stimulation amplitude decreased voiding efficiency. For summary data n=9 for 0.3 T to 1 T, n=7 for 1.5 T, 20 Hz, and n=6 for 1.5 T, 1 and 10 H.

FIG. 12: State-dependent stimulation in male cats.

A) Example cystometrograms without stimulation, with continuous stimulation, and with state-dependent stimulation. An inhibitory stimulus (10 Hz, 3 T) was used to promote bladder filling (inhibit bladder contractions). Two different excitatory stimuli, 33 Hz stimulation and motor bursting, were used to promote bladder emptying. Continuous stimulation increased bladder capacity but decreased voiding efficiency by 24%. B) State-dependent stimulation increased bladder capacity (n=6) relative to control trials. C) State-dependent stimulation increased voiding efficiency relative to continuous stimulation (p=0.003 for ANOVA test, p=0.028 for fill only, p=0.048 for 33 Hz, p<0.001 for motor bursting, n=5); in all experiments motor bursting increased voiding efficiency relative to control trials. Bladder capacities from all stimulation trials were averaged across experiments as the inhibitory stimulus was always 3 T, 10 Hz on the dorsal genital nerve (DGN).

Figure 13:
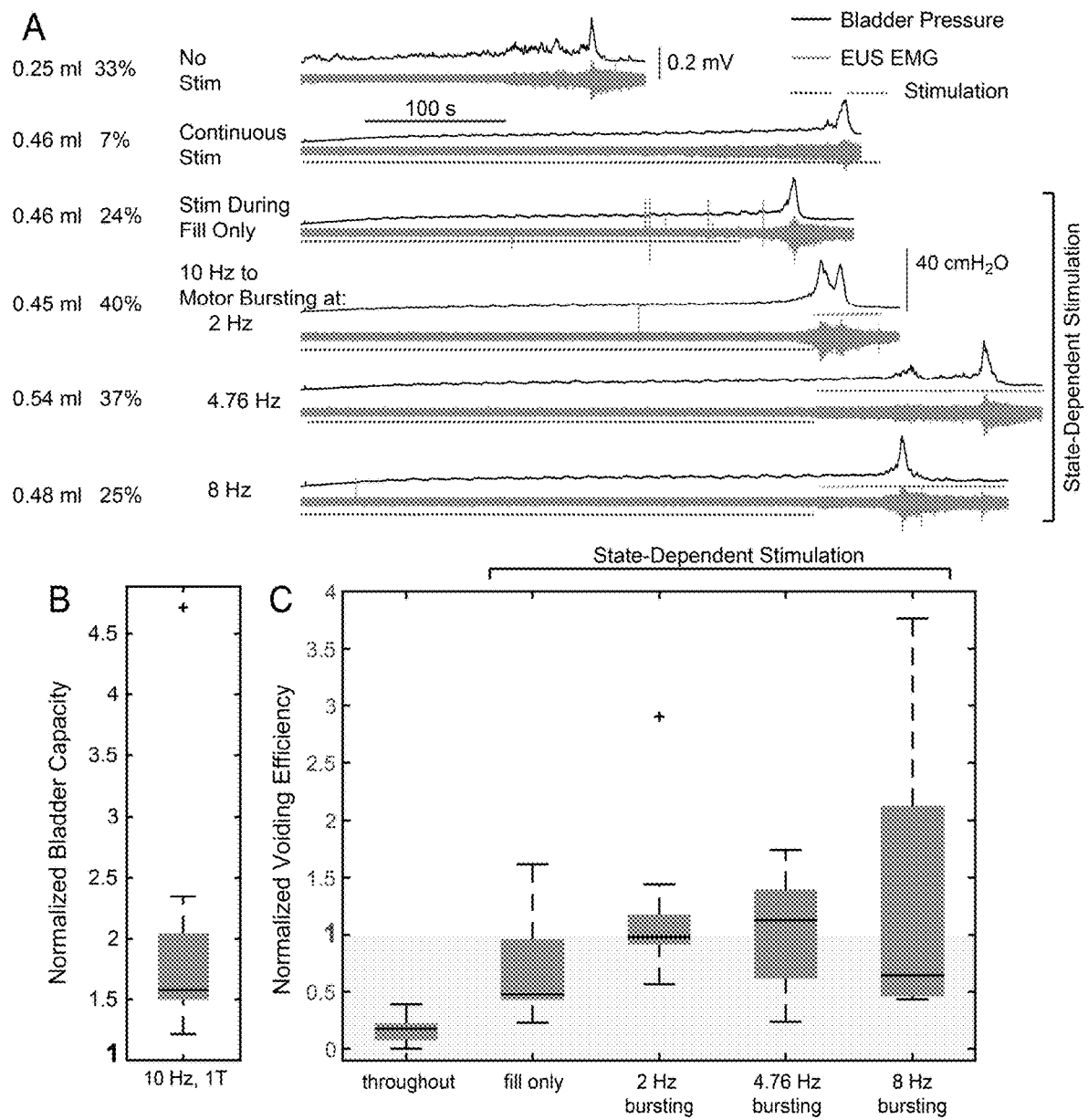

FIG. 13: State-dependent stimulation in the female rat (n=9) using electrical stimulation of the sensory pudendal nerve (10 Hz, 1 T) to inhibit bladder contractions (promote bladder filling) and either stimulus termination (fill-only condition) or motor bursting patterns to promote bladder emptying. A) Example cystometrograms from a single experiment. Lines below the EUS EMG traces demonstrate the duration of sensory pudendal stimulation. Lines above the EUS EMG traces demonstrate the duration of motor bursting stimulation. Values on the left are average bladder capacity and voiding efficiency data for trials of this type in this experiment. B) Normalized bladder capacity for all stimulation trials relative to controls. All relevant trials within an experiment were averaged together resulting in a single data point for each experiment. C) Normalized voiding efficiency for all stimulation conditions relative to controls. State-dependent stimulation increased voiding efficiency relative to continuous stimulation (p=0.023 for ANOVA, p=0.016 for fill-only, p=0.001 for 2 Hz, p=0.003 for 4.76 Hz, p=0.004 for 8 Hz, n=5).

FIG. 14: State-dependent stimulation in a female cat and side-by-side summary data from male and female cats. A) Example cystometrograms without stimulation, with continuous stimulation, and with state-dependent stimulation. Continuous stimulation increased bladder capacity but decreased voiding efficiency by 52% (Voiding efficiency was calculated as voided volume divided by the voided and residual volumes). B) State-dependent stimulation increased bladder capacity (n=6 males, 5 females) relative to control trials. C) State-dependent stimulation increased voiding efficiency relative to continuous stimulation; in all experiments motor bursting increased voiding efficiency relative to control trials. Experiment counts were n=6M,5F (M=male, F=female) for continuous stimulation, n=6M,4F for fill only stimulation, n=6M,4F for 33 Hz stimulation, n=5M,5F for motor bursting stimulation. Bladder capacities from all stimulation trials were averaged across experiments as the inhibitory stimulus was always 3 T, 10 Hz on the dorsal genital nerve (males) or sensory pudendal nerve (females).

DETAILED DESCRIPTION OF THE INVENTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The terms as used herein are given their conventional definition in the art as understood by the skilled person, unless otherwise defined below. In the case of any inconsistency or doubt, the definition as provided herein should take precedence.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising" or "having" certain elements are also contemplated as "consisting essentially of and "consisting of those certain elements.

Recitation of ranges of values herein are merely intended to serve as a shorthand method of referring individually to each separate value falling within the range, unless otherwise-Indicated herein, and each separate value is incorporated into the specification as if it were individually recited herein. For example, if a frequency range is stated as 1 Hz to 50 Hz, it is intended that values such as 2 Hz to 40 Hz, 10 Hz to 30 Hz, or 1 Hz to 3 Hz, etc., are expressly enumerated in this specification. These are only examples of what is specifically intended, and all possible combinations of numerical values between and including the lowest value and the highest value enumerated are to be considered to be expressly stated in this disclosure.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, rat, horse, cow, chickens, amphibians, reptiles, and the like.

As used herein, "electrode" is taken to mean any element capable of applying an electrical signal to the nerve.

As used herein, "stimulation of neural activity" may be an increase in the total signalling activity of the whole nerve, or that the total signalling activity of a subset of nerve fibres of the nerve is increased, compared to baseline neural activity in that part of the nerve. A "selective increase in neural activity", for example in the sensory fibres, causes a preferential increase in neural activity in the sensory fibres compared to any increase in neural signalling in the motor nerve fibres of the pudendal nerve. By way of further example, a selective increase in neural activity of the motor fibres causes a preferential increase in neural activity in the motor fibres compared to any increase in neural signalling in the sensory nerve fibres of the pudendal nerve.

"Phase-specific" or "state-dependent" stimulation are taken to mean that a different stimulation is applied depending on the ongoing and/or desired phase of the normal bladder activity cycle. The bladder activity cycle or micturition cycle is characterised by a filling phase (also referred to as a storage phase), followed by a triggering of the micturition, followed by a voiding phase (also referred to as the micturition phase). A normal bladder activity cycle is a bladder activity cycle characteristic of a healthy individual.

Application of an electrical signal in a "burst pattern" refers to application of the signal in a series of bursts. That is, the signal is applied for a burst—that is, a duration of time—followed by an interval in which no signal is applied. The interval is then followed by the signal being again applied for another burst, followed by another interval. The burst pattern is the combination of the burst for which the signal is applied followed by the interval during which no interval is applied.

The "ongoing phase" of bladder activity is the phase of the bladder activity cycle occurring at a particular given time. That a subject is in a given phase of the cycle can be indicated by a physiological parameter relevant to bladder activity, for example bladder pressure. For example, that a subject is in the filling phase may be indicated by increasing bladder pressure, or a sustained bladder pressure indicating that the bladder is at least partially filled. Triggering of micturition may be indicated by a sharp increase in bladder pressure. Other physiological parameters relevant to bladder activity include nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter (EUS), muscle activity in the external anal sphincter (EAS).

The "desired phase" of the bladder activity cycle is the phase of the bladder activity cycle of which the subject is desirous. The desired phase may depend on the behaviour of the subject, for example whether they are sleeping, at exercise, at work, etc. Similarly, the desired phase may depend on perceived levels of urinary comfort. For example, the subject may perceive discomfort due to the sensation of having a full bladder, and therefore be desirous of triggering micturition.

It will be appreciated that phase-specific stimulation can take into account both ongoing and desirous phases of the bladder activity cycle. For example, a first stimulating signal may be applied (e.g. to increase bladder capacity) during a filling phase indicated by increasing bladder pressure, and a second stimulating signal may be applied when the subject is desirous of beginning micturition (e.g. to trigger micturition), or during a voiding phase as indicated by a change in muscle activity in the EUS (e.g. to increase voiding efficiency).

As used herein "pudendal nerve" refers to the compound pudendal nerve and its associated branches, for example the dorsal nerve of the penis/clitoris (DNP) or the motor branch of the pudendal nerve.

As used herein, a "healthy individual" or "healthy subject" is an individual not exhibiting any disruption or perturbation of normal bladder activity.

As used herein, "bladder dysfunction" is taken to mean that the patient or subject is exhibiting disruption of bladder function compared to a healthy individual. Bladder dysfunction may be characterised by symptoms such as nocturia, increased urinary retention, increased incontinence, increased urgency of urination or increased frequency of urination compared to a healthy individual. Bladder dysfunction includes conditions such as overactive bladder (OAB), neurogenic bladder, stress incontinence, underactive bladder (UAB), and urinary retention.

Treatment of bladder dysfunction, as used herein may be characterised by any one or more of a reduction in number of incontinence episodes, a decrease in urgency of urination, a decrease in frequency of urination, an increase bladder capacity, an increase in bladder voiding efficiency, a decrease in urinary retention, a change in external urethral sphincter (EUS) activity towards that of a healthy individual, and/or a change in the pattern of action potentials or activity of the pudendal nerve towards that of a healthy individual.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a subject when the value for that parameter exhibited by the subject at the time of detection is determined. A detector is any element able to make such a determination.

A "predefined threshold value" for a physiological parameter is the value for that parameter where that value or beyond must be exhibited by a subject or subject before the intervention is applied. For any given parameter, the threshold value may be defined as a value indicative of a pathological state (e.g. the subject is experiencing abnormal retention of urine) or a particular physiological state (e.g. the subject having a full bladder), or a particular behavioural state (e.g. the subject wishes to begin voiding/micturition). Examples of such predefined threshold values include: bladder pressure abnormal compared to a healthy individual, bladder pressure indicative of bladder at or near capacity, abnormal peripheral nerve activity (for example, pudendal nerve, hypogastric nerve or pelvic nerve) compared to a healthy individual, abnormal EUS activity compared to a healthy individual (for instance an increase in EUS activity). Such a threshold value for a given physiological parameter is exceeded if the value exhibited by the subject is beyond the threshold value—that is, the exhibited value is a greater departure from the normal or healthy value for that parameter than the predefined threshold value.

The measurable physiological parameter may comprise an action potential or pattern of action potentials in one or more nerves of the subject, wherein the action potential or pattern of action potentials is associated with bladder dysfunction. Suitable nerves in which to detect an action potential or pattern of action potentials include a pudendal nerve, a pelvic nerve and/or a hypogastric nerve. In a particular embodiment, the measurable physiological parameter comprises the pattern of action potentials in the pudendal nerve.

The measurable physiological parameter may be muscle electromyographic activity, wherein the electromyographic activity is indicative of the level of activity in the muscle. Such activity could typically be measured from the bladder detrusor muscle, the internal urethral sphincter, the external urethral sphincter, and the external anal sphincter.

As used herein, "implanted" is taken to mean positioned within the subject's body. Partial implantation means that only part of the apparatus is implanted—i.e. only part of the apparatus is positioned within the subject's body, with other elements of the apparatus external to the subject's body. Wholly implanted means that the entire apparatus is positioned within the subject's body. For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the subject's body.

In accordance with a first aspect of the invention, there is provided an apparatus for stimulating neural activity in a pudendal nerve of a subject, the apparatus comprising: at least one primary electrode configured to apply a first electrical signal to said nerve; and a controller coupled to said primary electrode(s) and controlling the first electrical signal to be applied thereby, wherein said controller is configured to cause said at least one primary electrode to apply said first electrical signal that stimulates neural activity in the pudendal nerve to produce an increase in bladder capacity, wherein the first electrical signal comprises an AC waveform having a frequency in the range of from 0.1-50 Hz and wherein the first electrical signal has an amplitude in the range 0.05 to 10 T. In certain embodiments the first electrical signal has an amplitude in the range 0.1 to 10 T.

"T" is a measure of relative stimulation intensity. Relative stimulation intensity can be expressed as multiples (0.1, 0.8, 1, 2, 5, etc.) of "T". "T" represents the threshold stimulation intensity to evoke a motor response. For example, "1 T" is defined as the threshold stimulation intensity required to evoke a motor response—in particular, as used herein "T" may be defined as the threshold amplitude required to evoke a reflex electromyogram (EMG) response in the external urethral sphincter (EUS) when the electrical signal is applied to the pudendal nerve. As another example, the term "1 T" may be defined at the threshold amplitude required to evoke a reflex EMG response in the external anal sphincter (EAS). The type of motor response measured may dependent on the subject. For example, in rats, the EUS is measured. In cats, the EAS is measured. By way of further example, "1 T" may be defined in humans as the threshold amplitude required to evoke a perceptible sensation.

Determining "T" as described herein provides a calibration baseline able to be transferred between individuals and/or species (e.g., rats vs. cats). T determined by either EUS or EAS provides a useful measure for amplitude normalization between individuals and/or species. For example, T may be determined as follows: a low frequency electrical signal (e.g., 1 Hz) is applied and the intensity of stimulation is increased (either by increasing the voltage or the current of the signal, preferably the current) until the pudendal nerve stimulation produces a reflex EMG response in the EUS (or EAS). This stimulation intensity is designated T. The absolute threshold stimulation intensity may vary across individuals and/or species due to inherent variation, positioning and type of the electrode, etc., and therefore subsequent experimental or therapeutic intensities are designated as multiples of T to provide equivalent relative stimulation intensities.

The desired stimulation intensity (i.e. the desired multiple of threshold intensity "T") can be achieved through controlled variation of the current or voltage of the signal, preferably the current.

In some embodiments the first electrical signal is a "low intensity" signal. In such embodiments, the first electrical signal has an amplitude in the range from 0.05 T to <2.0 T. In additional embodiment, the first signal has an amplitude in the range from 0.3 T to <2 T. In certain embodiments, the first electrical signal has an amplitude value of from 0.5 T to 1.5 T. In some embodiments, the first electrical signal has an amplitude of 0.05, 0.1, 0.2, 0.3, 0.4, 0.5 0.6, 0.7, 0.8, 0.9, 1.0, 1.1, 1.2, 1.3, 1.4, 1.5, 1.6, 1.7, 1.8, 1.9, or 2.0 T. In some embodiments, the electrical signal has a T value of 1 T-1.5 T. In other embodiments, the first electrical signal has an amplitude of 1 T. In other embodiments, the first electrical signal has an amplitude of 1.5 T.

In other embodiments the first electrical signal is a "high intensity" signal. In such embodiments, the first electrical signal has an amplitude in the range from 2 T to 10 T. In some embodiments, the first electrical signal comprises has an amplitude value of from 2 T to 4 T. In such embodiments, the first electrical signal has an amplitude of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 T. In certain embodiments, the first electrical signal has an amplitude of 3 T.

In other embodiments, the first electrical signal has an amplitude in the range of from 0.1 to 20 mA. In certain embodiments, the first electrical signal has an amplitude in the range of from 0.1-10 mA, optionally 0.1-5 mA, optionally 0.1-1 mA, optionally 100-500 µA, optionally 100-400 µA. In certain embodiments, the first electrical signal has an amplitude of 100 µA, 200 µA, or 400 µA.

In certain embodiments, the apparatus may comprise two or more primary electrodes, where each primary electrode is configured to apply the first electronic signal. In certain such embodiments, the apparatus comprises two primary electrodes suitable for bilateral positioning.

In certain embodiments, the first electrical signal stimulates neural activity in sensory fibres of the pudendal nerve, optionally selectively stimulates neural activity in sensory fibres of the pudendal nerve, so as to produce an increase in bladder capacity.

In certain embodiments, the first electronic signal comprises an AC waveform having a frequency in the range of from 1-50 Hz. In certain embodiments the first electronic signal comprises an AC waveform having a frequency in the range of 1-20 Hz, for example 1, 2, 3, 4, 5, 6, 7, 8, 9, 10, 11, 12, 13, 14, 15, 16, 17, 18, 19, 20 Hz. In certain embodiments wherein the first signal is a "low intensity" signal, the first electronic signal has a frequency of 10 or 20 Hz. In certain embodiments wherein the first signal is a "high intensity" signal, the first electronic signal has a frequency of 10 Hz.

It will be appreciated by the skilled person that an electronic signal "comprising" an indicated frequency may have other frequency components as part of the signal. In certain preferred embodiments of all aspects where a signal comprises an indicated frequency, the indicated frequency is the dominant frequency component of the signal.

In another embodiment, the controller is configured to cause a second electrical signal to be applied, wherein said second electrical signal stimulates neural activity in the pudendal nerve to produce an increase in voiding efficiency. In some embodiments the second electrical signal comprises an AC waveform having a frequency higher than the frequency of the first electrical signal.

In certain such embodiments, the second signal has a frequency in the range of from 5-50 Hz, optionally 20-40 Hz. In certain embodiments, the second signal has a frequency of 20-50 Hz. In certain embodiments, the second signal has a frequency of 30-40 Hz Hz. In certain embodiments, the second electrical signal has a frequency of 33 Hz. In certain embodiments, the second electrical signal has a frequency of 40 Hz. In certain such embodiments, the second electronic signal stimulates neural activity in sensory fibres of the pudendal nerve.

In some embodiments, the second electronic signal is applied by the at least one primary electrodes. In certain alternative embodiments, the second electrical signal is applied by at least one secondary electrode(s) coupled to said controller, said controller controlling the signal to be applied thereby.

In another embodiment, the apparatus further comprises at least one secondary electrode configured to apply a second electrical signal to said nerve and coupled to said controller, said controller controlling the signal to be applied thereby, wherein said controller is configured to cause said secondary electrode to apply said second electrical signal that stimulates neural activity in the pudendal nerve to produce an increase in voiding efficiency, wherein the second electrical signal comprises an AC waveform and wherein said controller is configured to cause said second electrical signal to be applied in a burst pattern.

In certain embodiments, the burst pattern comprises a signal burst having a duration of from 50 ms to 1000 ms. In certain embodiments, the burst pattern comprises a signal burst having a duration of 100 ms.

In certain embodiments, the burst pattern comprises a signal burst having a duration from 50 ms to 1000 ms repeated at an interval of from 0.125 s to 2 s. In certain embodiments, the burst pattern comprises a signal burst having a duration from 50 ms to 1000 ms repeated at an interval of from 0.2 s to 2 s. In certain embodiments, the burst pattern comprises a signal burst having a duration of 100 ms repeated at an interval of 0.5 s.

In certain embodiments, the burst pattern consists of a signal burst having a duration from 50 ms to 1000 ms repeated at an interval of from 0.125 s to 2 s. In certain embodiments, the burst pattern consists of a signal burst having a duration from 50 ms to 1000 ms repeated at an interval of from 0.2 s to 2 s. In certain embodiments, the burst pattern consists of a signal burst having a duration of 100 ms repeated at an interval of 0.5 s.

In some embodiments, the second electrical signal applied in a burst pattern comprises a signal burst repeated at a frequency in the range of from 0.5 to 20 Hz. For example, a burst patent comprising a signal burst repeated at a frequency of 2 Hz would repeat the signal burst at 0.5 s intervals (FIG. 10F). In some embodiments, the second electrical signal applied in a burst pattern comprises a signal burst repeated at a frequency in the range of 2 to 20 Hz. In some embodiments, the second electrical signal applied in a burst pattern comprises a signal burst repeated at a frequency in the range of 2 to 10 Hz. In such embodiments the signal burst comprises an AC waveform.

In one embodiment, the second electrical signal comprises a signal burst repeated at a frequency comprising 10 Hz, optionally wherein the second electrical signal comprises an AC waveform repeated at a frequency of 10 Hz. In another embodiment, the second electrical signal is repeated at a frequency comprising 2 Hz, optionally wherein the second electrical signal is repeated at a frequency of 2 Hz. In another embodiment, the second electrical signal is repeated at a frequency comprising 4.76 Hz, optionally wherein the second electric signal is repeated at a frequency of 4.76 Hz. In another embodiment, the second electrical signal is repeated at a frequency comprising 8 Hz, optionally wherein the second electric signal is repeated at a frequency of 8 Hz.

In certain embodiments, the second electrical signal applied in a burst pattern comprises a signal burst wherein the signal burst comprises an AC waveform having a frequency in the range of from 20-50 Hz. In certain embodiments, the signal burst comprises an AC waveform having a frequency of 30-40 Hz. In certain such embodiments, the signal burst has a frequency of 40 Hz.

In some embodiments, the burst pattern consists of from 1 to 10 pulses per signal burst. In some embodiments, the burst pattern consists of from 1 to 5 pulses per signal burst. In some embodiments, the burst pattern consists of 3 pulses per signal burst. In such embodiments, the duration of the signal burst is thus determined by the frequency of the AC waveform.

In other embodiments where a second electrical signal is (to be) applied, the second electrical signal comprises an AC waveform having an amplitude in the range of 0.5-4 T. In some embodiments, the second electrical signal comprises an AC waveform having an amplitude in the range 1-3 T. In some embodiments, the second electrical signal comprises an amplitude of about 3 T. In other embodiments wherein the second electrical signal is applied in a burst pattern, the second electrical signal comprises an amplitude of 1 T. In other embodiments where the second electrical signal is applied in a burst pattern, the second electrical signal comprises an amplitude of 1.8-2.3 T.

In certain embodiments, the second electrical signal has an amplitude of 0.1-20 mA, optionally 0.1-10 mA, optionally 0.1-5 mA, optionally 0.1-1 mA, optionally 100-500 µA, optionally 100-400 µA. In certain embodiments, the second electrical signal has an amplitude of 100 µA, 200 µA, or 400 µA.

In other embodiments, the second electrical signal stimulates neural activity in motor fibres of the pudendal nerve, optionally selectively stimulates neural activity in motor fibres of the pudendal nerve, so as to produce an increase in voiding efficiency. In such embodiments, the secondary electrode(s) may be configured to be positioned on a motor branch of the pudendal nerve.

In certain embodiments, the apparatus may comprise two or more secondary electrodes, where each primary electrode is configured to apply the second electronic signal. In certain such embodiments, the apparatus comprises two secondary electrodes suitable for bilateral positioning.

The following embodiments apply equally to the first and second electronic signals unless specified otherwise.

In certain embodiments, the AC waveform is a biphasic waveform, optionally a charge-balanced biphasic waveform. In certain such embodiments, the waveform may be symmetrical or asymmetrical. In certain such embodiments, each phase of the biphasic waveform has a phase duration from 0.005 ms to 2 ms, optionally 0.01 to 1 ms, optionally 0.05 to 0.5 ms, optionally 0.05 to 0.2 ms, optionally 0.1 ms. In certain embodiments, each phase of a biphasic waveform is of equal duration. In certain alternative embodiments, each phase is of a different duration.

The AC waveform may be selected from sinusoidal, triangular, square or a complex waveform.

In certain embodiments, the apparatus further comprises a detector to detect one or more physiological parameters in the subject. Such a detector may be configured to detect one physiological parameter or a plurality of physiological parameters The detected physiological parameter(s) are selected from nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

In such embodiments, the controller is coupled to the detector configured to detect a physiological parameter and causes the controller to cause the first electrical signal to be applied when the physiological parameter is detected to be meeting or exceeding a first predefined threshold value, for example when the detected value indicates that the subject is in the filling phase of the micturition cycle. In certain embodiments, the controller causes the first electronic signal to be stopped when the detector detects onset of a bladder voiding phase.

Where a second electronic signal is to be applied, the detector may cause the controller to cause the second electrical signal to be applied when a physiological parameter is detected to be meeting or exceeding a second predefined threshold value, for example when the detected value indicates that the subject is in the voiding phase of the micturition cycle.

It will be appreciated that any two or more of the indicated physiological parameters may be detected in parallel or consecutively. For example, in certain embodiments, the controller is coupled to a detector or detectors configured to detect the pattern of action potentials in the pudendal nerve at the same time as the bladder pressure in the subject.

In addition, or as an alternative to a detector, the apparatus may comprise an input element. In such embodiments, the input element allows the subject to enter data regarding their behaviour and/or desires. For example, the input element may allow the subject to enter that they desire to begin bladder voiding (i.e. intend to begin urinating). In such embodiments, the controller is configured to cause a signal to be applied that produces a physiological response appropriate to the data input—for example, in the case of the intention to urinate being indicated, the signal may increase voiding efficiency. By way of further example, the input element may also allow the subject to enter data indicative of behaviour in which storage phase is appropriate (e.g. sleeping or following urination, where it is desirous to promote storage). In response to such data being entered via the input element, the controller causes a signal to be applied that produces a physiological response appropriate for improved storage, for example increased bladder capacity. The input element may be connected directly to the controller, or be in wireless communication as a remote component, for example a component carried by the subject. Such arrangements and configurations are discussed in further detail below.

In certain embodiments, the apparatus further comprises one or more power supply elements, for example a battery, and/or one or more communication elements.

In certain embodiments, the apparatus is suitable for at least partial implantation into the subject, optionally full implantation into the subject.

In a second aspect, the present disclosure provides a method of treating bladder dysfunction in a subject comprising:

i. implanting in the subject an apparatus according to the invention;

ii. positioning at least one primary electrode of the apparatus in signalling contact with a pudendal nerve of the subject and, when the apparatus comprises at least one secondary electrode, positioning said at least one secondary electrode of the apparatus in signalling contact with a pudendal nerve of the subject;

iii. activating the apparatus to apply an electrical signal to the pudendal nerve of the subject as caused by the controller. The apparatus is activated when the apparatus is in an operating state such that the signal will be applied as determined by the controller.

In certain embodiments the first signal is applied during a filling phase and the second signal applied during a voiding phase. In certain embodiments, application of the first electronic signal results in an increase in bladder capacity. In certain embodiments in which the apparatus is configured to apply a second electronic signal, application of the second electronic signal results in an increase in voiding efficiency.

In certain embodiments, the method comprises implanting an apparatus according to the invention having at least two primary electrodes, and optionally at least two secondary electrodes, and positioning the electrodes bilaterally—that is, one primary electrode in signalling contact with the left pudendal nerve, and one primary electrode in signalling contact with the right pudendal nerve.

In certain embodiments, the method is a method for treating overactive bladder, neurogenic bladder, mixed urge and stress incontinence, under active bladder (UAB), urinary retention, or detrusor hyperactivity with impaired contractility (DHIC).

Implementation of all aspects of the present disclosure (as discussed both above and below) will be further appreciated by reference to FIGS. 1A-1C.

Figure 1A:
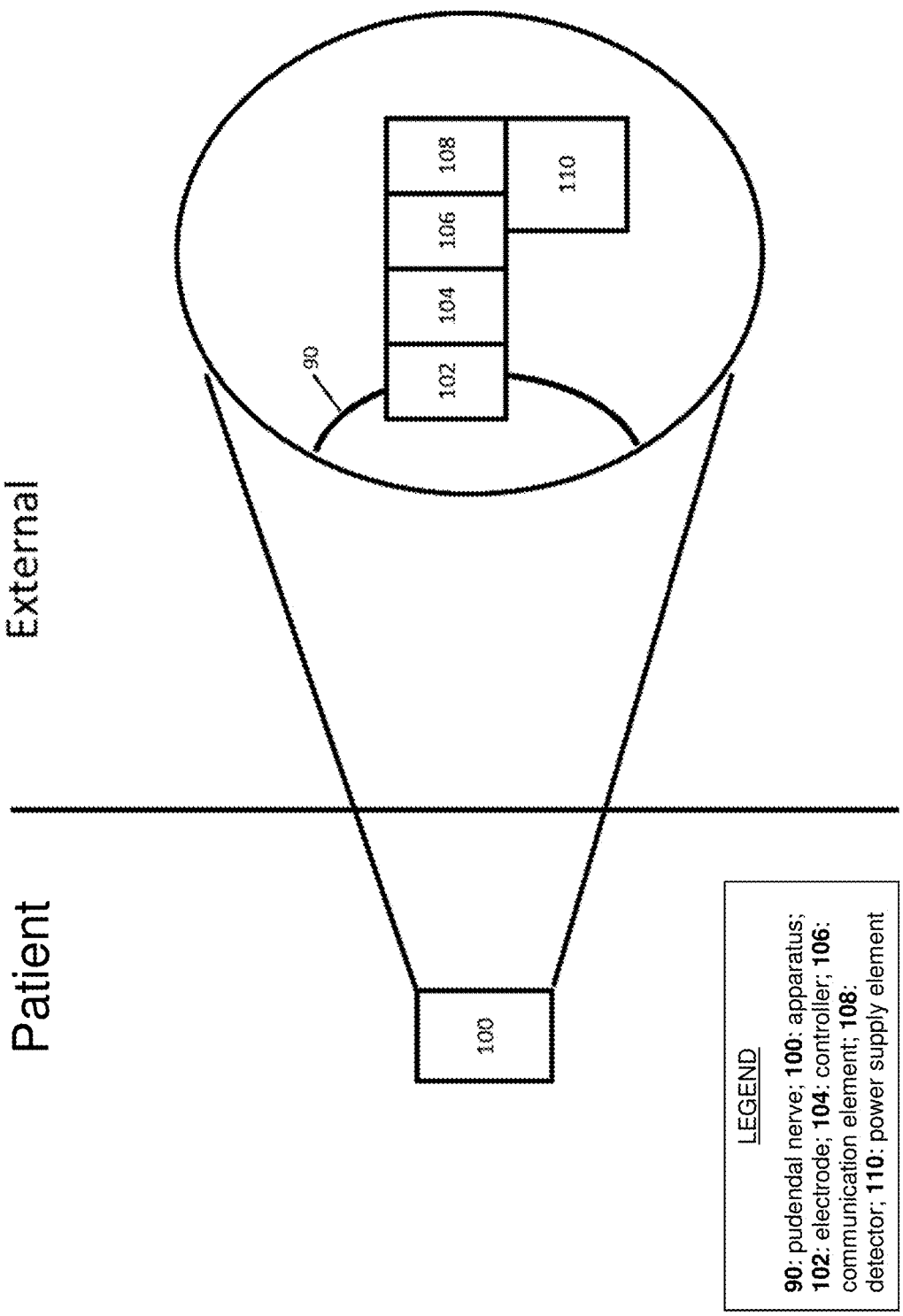
FIG. 1—Schematic drawings showing how apparatuses, devices and methods according to the invention can be put into effect.
Figure 1C:
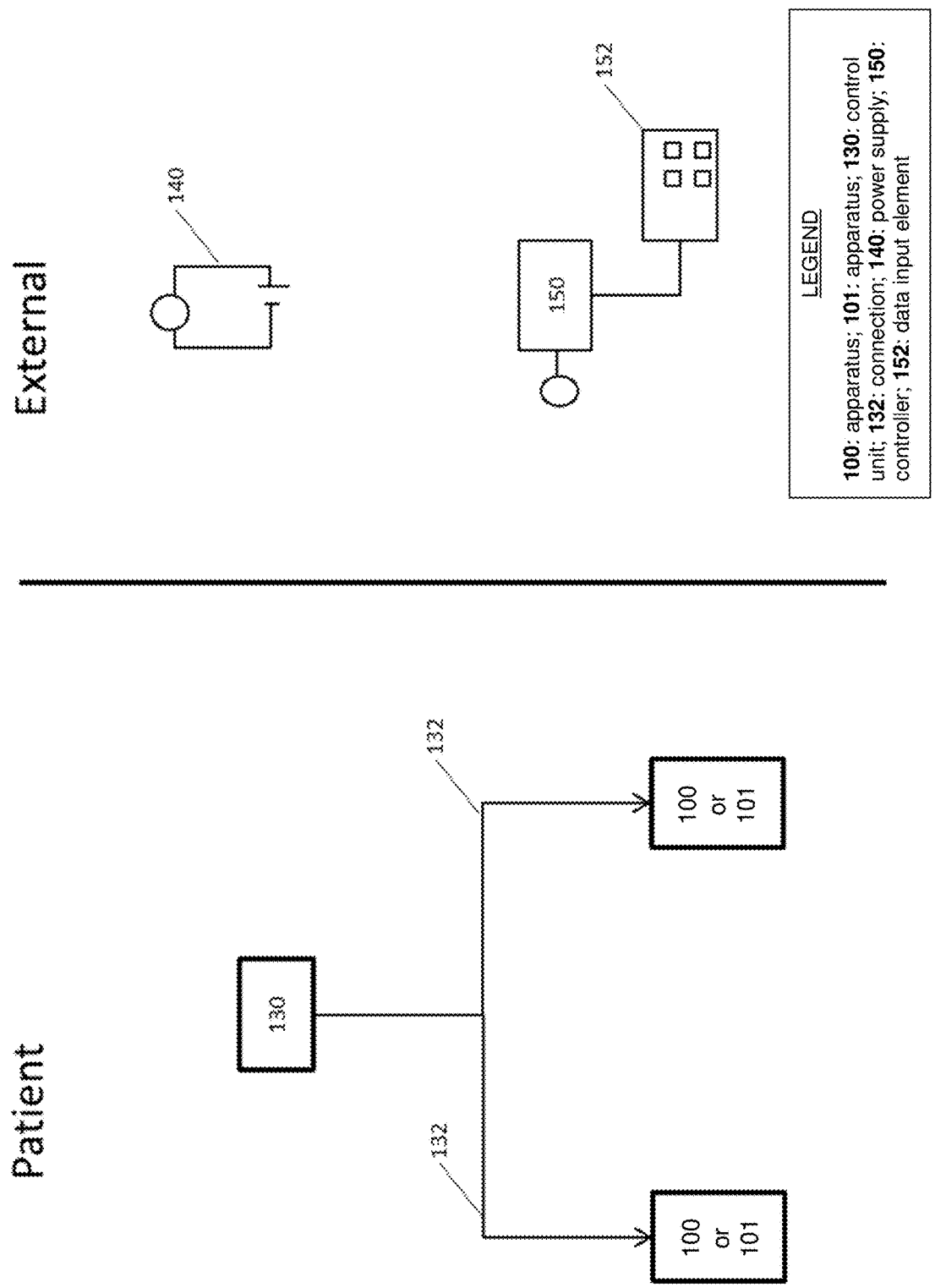

FIGS. 1A-1C show how the invention may be put into effect using one or more apparatuses which are implanted in, located on, or otherwise disposed with respect to a subject in order to carry out any of the various methods described herein. In this way, one or more apparatuses can be used to treat bladder dysfunction in a subject, by stimulating neural activity in a pudendal nerve.

In FIG. 1A a separate apparatus 100 is provided for unilateral neuromodulation, although as discussed above and below an apparatus could be provided for bilateral neuromodulation (101, FIGS. 1B and 1C). Each such apparatus may be fully or partially implanted in the subject, or otherwise located, so as to provide neuromodulation of the respective nerve or nerves. FIG. 1A also schematically shows in the cutaway components of one of the apparatuses 100, in which the apparatus comprises several elements, components or functions grouped together in a single unit and implanted in the subject. A first such element is an electrode 102 which is shown in proximity to a pudendal nerve 90 of the subject. The apparatus may optionally further comprise further electrodes (not shown) implanted proximally to the same or other pudendal nerve. Alternatively, the other pudendal nerve may be provided with a separate apparatus 100 or 101 (not shown). The primary electrode 102 may be operated by a controller 104. The apparatus may comprise one or more further elements such as a communication element 106, a detector 108, a power supply element 110 and so forth. Each apparatus 100 or 101 may operate independently, or may operate in communication with each other, for example using respective communication elements 106.

Each neuromodulation apparatus 100 or 101 may carry out the required stimulation in response to one or more control signals. Such a control signal may be provided by the controller 104 according to an algorithm independently, in response to output of one or more detector elements 108, and/or in response to communications from one or more external sources (for example an input element) received using the communications element. As discussed herein, the detector(s) could be responsive to a variety of different physiological parameters.

FIG. 1B illustrates some ways in which the apparatus of FIG. 1A may be differently distributed. For example, in FIG. 1B the apparatuses 101 comprise electrodes 102 implanted proximally to a pudendal nerve 90, but other elements such as a controller 104, a communication element 106 and a power supply 110 are implemented in a separate control unit 130 which may also be implanted in, or carried by the subject. The control unit 130 then controls the electrodes in both of the apparatuses via connections 132 which may for example comprise electrical wires and/or optical fibres for delivering signals and/or power to the electrodes.

In the arrangement of FIG. 1B one or more detectors 108 are located separately from the control unit, although one or more such detectors could also or instead be located within the control unit 130 and/or in one or both of the apparatuses 101. The detectors may be used to detect one or more physiological parameters of the subject, and the controller or control unit then causes the transducers to apply the first or second signal in response to the detected parameter(s), for example only when a detected physiological parameter meets or exceeds a predefined threshold value. Physiological parameters which could be detected for such purposes may be selected from nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

A variety of other ways in which the various functional elements could be located and grouped into the neuromodulation apparatuses, a control unit 130 and elsewhere are of course possible. For example, one or more sensors of FIG. 1B could be used in the arrangement of FIG. 1A or 1C or other arrangements.

FIG. 1C illustrates some ways in which some functionality of the apparatus of FIG. 1A or 1B is provided not implanted in the subject. For example, in FIG. 1C an external power supply 140 is provided which can provide power to implanted elements of the apparatus in ways familiar to the skilled person, and an external controller 150 provides part or all of the functionality of the controller 104, and/or provides other aspects of control of the apparatus, and/or provides data readout from the apparatus, and/or provides a data input element 152. The data input facility could be used by a subject or other operator in various ways, for example to input data relating to the behaviour of the subject and/or their desires (e.g. that they are in a voiding phase).

By way of further example, devices for stimulating nerve activity in the pudendal nerve are described in U.S. Pat. Nos. 7,571,000 and 8,396,555, each of which are incorporated herein by reference.

In a further aspect, the invention provides a method of treating bladder dysfunction in a subject comprising applying a first electrical signal to a pudendal nerve of the subject, wherein the first electrical signal comprises an AC waveform having a frequency in the range of from 0.1-50 Hz and wherein the first electrical signal has an amplitude in the range from 0.05 T to 10 T. In certain embodiments, the first electrical signal has an amplitude in the range from 0.1 T to 10 T.

In other embodiments, application of the method is mediated using an apparatus according to the present disclosure.

In another embodiment, first electrical signal is applied to the pudendal nerve during a bladder filling phase, wherein application of said first electrical signal increases bladder capacity.

In another embodiment, application of the first electrical signal is stopped at the onset of a bladder voiding phase. Where the method is performed by an apparatus as described herein, such halting of the first electrical signal may be caused by voiding being detected by the apparatus or may be caused by the subject indicating via an input element that voiding phase had commenced.

In yet another embodiment, the first electrical signal stimulates neural activity in sensory fibres of the pudendal nerve, optionally selectively stimulates neural activity in sensory fibres of the pudendal nerve, so as to produce an increase in bladder capacity.

In some embodiments the first electronic signal comprises an AC waveform having a frequency 1 Hz to about 50 Hz. In some embodiments, the first electrical signal applied comprises an AC waveform having a frequency of 1 to about 45 Hz. In yet other embodiments, the first electrical signal applied comprises an AC waveform having a frequency in the range of from 20 to about 40 Hz. In other embodiments, the first electrical signal comprises a frequency in the range of 2 to about 10 Hz.

In certain embodiments, the application of a second electrical signal, which has a frequency 33 Hz, provides a positive voiding effect (i.e., increased voiding efficiency) in a male subject and a negative voiding effect (i.e., decreased voiding efficiency) in a female subject. In certain embodiments, the application of the first signal and no second signal provides a positive voiding effect in a male subject and a negative voiding effect in a female subject In another embodiment, the method further comprises applying a second electrical signal to a pudendal nerve of the subject, wherein the second electrical signal comprises an AC waveform and is applied in a burst pattern.

In certain embodiments, the burst pattern comprises a signal burst having a duration of from 50 ms to 1000 ms. In certain embodiments, the burst pattern comprises a signal burst having a duration of 100 ms.

In some embodiments, the second electrical signal applied in a burst pattern comprises a signal burst repeated at a frequency in the range of from 0.5 to 20 Hz. For example, a burst patent comprising a signal burst repeated at a frequency of 2 Hz would repeat the signal burst at 0.5 s intervals (FIG. 10F). In some embodiments, the second electrical signal applied in a burst pattern comprises a signal burst repeated at a frequency in the range of 2 to 20 Hz. In some embodiments, the second electrical signal applied in a burst pattern comprises a signal burst repeated at a frequency in the range of 2 to 10 Hz. In such embodiments, the signal burst comprises an AC waveform.

In some embodiments, the burst pattern consists of a signal burst having a duration from 50 ms to 1000 ms repeated at an interval of from 0.125 s to 2 s. In some embodiments, the burst pattern consists of a signal burst having a duration from 50 ms to 1000 ms repeated at an interval of from 0.2 s to 2 s. In certain embodiments, the burst pattern consists of a signal burst having a duration of 100 ms repeated at an interval of 0.5 s.

In some embodiments, the second electrical signal applied in a burst pattern comprises an AC waveform repeated at a frequency in the range of from 0.5 to 20 Hz. In some embodiments, the second electrical signal applied in a burst pattern comprises an AC waveform repeated at a frequency in the range of 2 to 20 Hz. In some embodiments, the second electrical signal applied in a burst pattern comprises an AC waveform repeated at a frequency in the range of 2 to 10 Hz.

In one embodiment, the second electrical signal is applied in a burst pattern comprising an AC waveform repeated at a frequency comprising 10 Hz, optionally wherein the second electrical signal comprises an AC waveform repeated at a frequency of 10 Hz. In another embodiment, the second electrical signal is repeated at a frequency comprising 2 Hz, optionally wherein the second electrical signal is repeated at a frequency of 2 Hz. In another embodiment, the second electrical signal is repeated at a frequency comprising 4.76 Hz, optionally wherein the second electric signal is repeated at a frequency of 4.76 Hz. In another embodiment, the second electrical signal is repeated at a frequency comprising 8 Hz, optionally wherein the second electric signal is repeated at a frequency of 8 Hz.

In some embodiments, the second electrical signal applied in a burst pattern comprises a signal burst comprising an AC waveform having a frequency in the range of from 20-50 Hz. In certain embodiments, the second electrical signal applied in a burst pattern comprises a signal burst comprising an AC waveform having a frequency of 30-40 Hz. In certain such embodiments, the second electronic signal has a frequency of 40 Hz.

The second electrical signal applied in a burst pattern may be at a frequency of 40 Hz applied in bursts at different intervals, for example 0.125 seconds, 0.21 seconds and 0.5 seconds. In another embodiment, the second electrical signal is repeated at a frequency of 2 Hz. In another embodiment, the second electric signal is repeated at a frequency of 4.76 Hz. In another embodiment, the second electric signal is repeated at a frequency of 8 Hz.

In some embodiments, the burst pattern consists of from 1 to 10 pulses per signal burst. In some embodiments, the burst pattern consists of from 1 to 5 pulses per signal burst. In some embodiments, the burst pattern consists of 3 pulses per signal burst. In such embodiments, the duration of the signal burst is thus dictated by the frequency of the AC waveform.

In another embodiment the second electrical signal has an amplitude value of from 0.5 T to 4 T, optionally 1-3 T. In certain embodiments wherein the second electrical signal has a frequency higher than the first electrical signal, the second electrical signal has an amplitude of 3 T. In certain embodiments wherein the second electrical signal is applied in a burst pattern, the second electrical signal has an amplitude of 1.8-2.3 T.

In some embodiments, the second electrical signal has an amplitude of 0.1-20 mA, optionally 0.1-10 mA, optionally 0.1-5 mA, optionally 0.1-1 mA, optionally 100-500 µA, optionally 100-400 µA. In certain embodiments, the second electrical signal has an amplitude of 100 µA, 200 µA, or 400 µA.

In another embodiment, the second electrical signal stimulates neural activity in motor fibres of the pudendal nerve, optionally selectively stimulates neural activity in motor fibres of the pudendal nerve, so as to produce an increase in voiding efficiency. In certain such embodiments, the second electrical signal is applied to a motor branch of the pudendal nerve.

The following embodiments apply equally to the first and second electronic signals unless specified otherwise.

In certain embodiments, the AC waveform is a biphasic waveform, optionally a charge-balanced biphasic waveform. In certain such embodiments, the waveform may be symmetrical or asymmetrical. In certain such embodiments, each phase of the biphasic waveform has a phase duration from 0.005 ms to 2 ms, optionally 0.01 to 1 ms, optionally 0.05 to 0.5 ms, optionally 0.05 to 0.2 ms, optionally 0.1 ms. In certain embodiments, each phase of a biphasic waveform is of equal duration. In certain alternative embodiments, each phase is of a different duration.

The AC waveform may be selected from sinusoidal, triangular, square or a complex waveform.

In certain embodiments, treatment of bladder dysfunction, for example overactive bladder, may be characterised by a combination of an increase in bladder capacity during filling periods and an increase in voiding efficiency for voiding periods.

In certain embodiments, the method is a method for treating overactive bladder, neurogenic bladder, underactive bladder (UAB), urinary retention, or detrusor hyperactivity with impaired contractility (DHIC).

As demonstrated in the Examples, stimulation of the pudendal nerve in accordance with the invention can improve bladder function during subsequent micturition cycles, even when stimulation is no longer being applied. This presents a significant advantage, as therapeutic benefit can be achieved across multiple micturition cycles as a result of stimulation in only one. This results in reduced power demand and less impact on the patient without a loss of therapeutic benefit. Therefore, in certain embodiments, the first electronic signal is applied no more frequently than alternate micturition cycles—that is, no more frequently than every two micturition cycles—for example, every 2, every 3, or every 4 micturition cycles. In certain embodiments, the first electronic signal is applied no more frequently than every three micturition cycles. In certain embodiments the first electronic signal is applied every two micturition cycles—i.e. every other filling phase. By way of explanation, in such embodiments, the first electronic signal is applied during the filling phase of one cycle. The signal may be then stopped for the voiding phase of that cycle and is not applied during the next filling phase or voiding phase—i.e. for a complete cycle. Once a complete micturition cycle has occurred with no first electronic signal being applied, the first electronic signal is then applied during the subsequent filling phase.

In a further aspect the invention provides a neuromodulation system, the system comprising a plurality of apparatuses according to the invention. In such a system, each apparatus may be arranged to communicate with at least one other apparatus, optionally all apparatuses in the system. In certain embodiments, the system is arranged such that, in use, the apparatuses are positioned to bilaterally stimulate the pudendal nerves of a patient.

In such embodiments, the system may further comprise additional components arranged to communicate with the apparatuses of the system, for example a processor, a data input facility, and/or a data display module. In certain such embodiments, the system further comprises a processor. In certain such embodiments, the processor is comprised within a mobile device (for example a smart phone) or computer.

In a further aspect, the invention provides a pharmaceutical composition comprising a compound for treating bladder dysfunction, for use in a method of treating bladder dysfunction in a subject, wherein the method is a method according to the invention, the method further comprising the step of administering an effective amount of the pharmaceutical composition to the subject. It is a preferred embodiment that the pharmaceutical composition is for use in a method of treating bladder dysfunction wherein the method comprises applying a signal to a part or all of a pudendal nerve of said patient to stimulate the neural activity of said nerve in the patient, the signal being applied by a neuromodulation apparatus.

In a further aspect, the invention provides a pharmaceutical composition comprising a compound for treating bladder dysfunction, for use in treating bladder dysfunction in a subject, the subject having an apparatus according to the invention implanted. That is, the pharmaceutical composition is for use in treating a subject that has had an apparatus as described according to the first aspect implanted. The skilled person will appreciate that the apparatus has been implanted in a manner suitable for the apparatus to operate as described. Use of such a pharmaceutical composition in a patient having an apparatus according to the first aspect implanted will be particularly effective as it permits a cumulative or synergistic effect as a result of the combination of the compound for treating bladder dysfunction and apparatus operating in combination.

In certain embodiments of these aspects, the compound for treating bladder dysfunction is selected from an antimuscarinic compound and a β-adrenergic receptor agonist, optionally a β3-adrenergic receptor agonist. In certain embodiments, the antimuscarinic compound is selected from darifenacin, hyoscyamine, oxybutynin, tolterodine, solifenacin, trospium, or fesoterodine. In certain embodiments, the β-adrenergic receptor agonist is a β3-adrenergic receptor agonist, for example mirabegron. In certain embodiments, the pharmaceutical composition is for use in treating OAB.

In certain embodiments, the pharmaceutical composition may comprise a pharmaceutical carrier and, dispersed therein, a therapeutically effective amount of the compounds for treating bladder dysfunction. The composition may be solid or liquid. The pharmaceutical carrier is generally chosen based on the type of administration being used and the pharmaceutical carrier may for example be solid or liquid. The compounds of the invention may be in the same phase or in a different phase than the pharmaceutical carrier.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds for treating bladder dysfunction may be admixed with pharmaceutically inert, inorganic or organic excipients. Examples of suitable excipients include lactose, maize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose. For injectable solutions, excipients include, for example, water, alcohols, polyols, glycerine and vegetable oil. For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

Thus, a pharmaceutical formulation for oral administration may, for example, be granule, tablet, sugar coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The compound may also be administered in the form of a suppository or pessary or may be applied topically in the form of a lotion, solution, cream, ointment or dusting powder.

In a preferred embodiment of all aspects of the invention, the subject or subject is a mammal, more preferably a human. In certain embodiments, the subject or subject is suffering from bladder dysfunction, for example OAB.

The foregoing detailed description has been provided by way of explanation and illustration and is not intended to limit the scope of the appended claims. Many variations in the presently preferred embodiments illustrated herein will be apparent to one of ordinary skill in the art and remain within the scope of the appended claims and their equivalents.

EXAMPLES

I. Experimental Dataset 1

The following experimental methods were used throughout Examples 1-5 discussed below.

Surgical Preparation and Equipment Setup

Female Wistar rats (n=18) weighing between 237 and 296 g were anesthetized with urethane (1.2 g/kg SC, supplemented as necessary). Body temperature was monitored using an esophageal temperature probe and maintained at 36-38° C. with a water blanket. Heart rate and arterial blood oxygen saturation levels were monitored using a pulse oximeter (Nonin Medical Inc., 2500A VET).

For cystometrogram (CMG) measurements, the bladder was exposed via a midline abdominal incision. A PE-90 catheter, the tip of which was heated to create a collar, was inserted into the bladder lumen through a small incision in the apex of the bladder dome and secured with a 6-0 silk suture. The abdominal wall was closed in layers with 3-0 silk suture. The bladder catheter was connected via a 3-way stopcock to an infusion pump (Braintree Scientific Inc., BS-8000 or Harvard Apparatus PHD 4400) and to a pressure transducer (ArgoTrans, ArgonMedical Devices Inc., Plano, Tex.) connected to a bridge amplifier and filter (13-6615-50, Gould Instruments, Valley View, Ohio) for measuring intravesical pressure (IVP). Data were sampled at 1 kHz using a PowerLab system (AD Instruments, Colorado Springs, Colo.).

Figure 2:
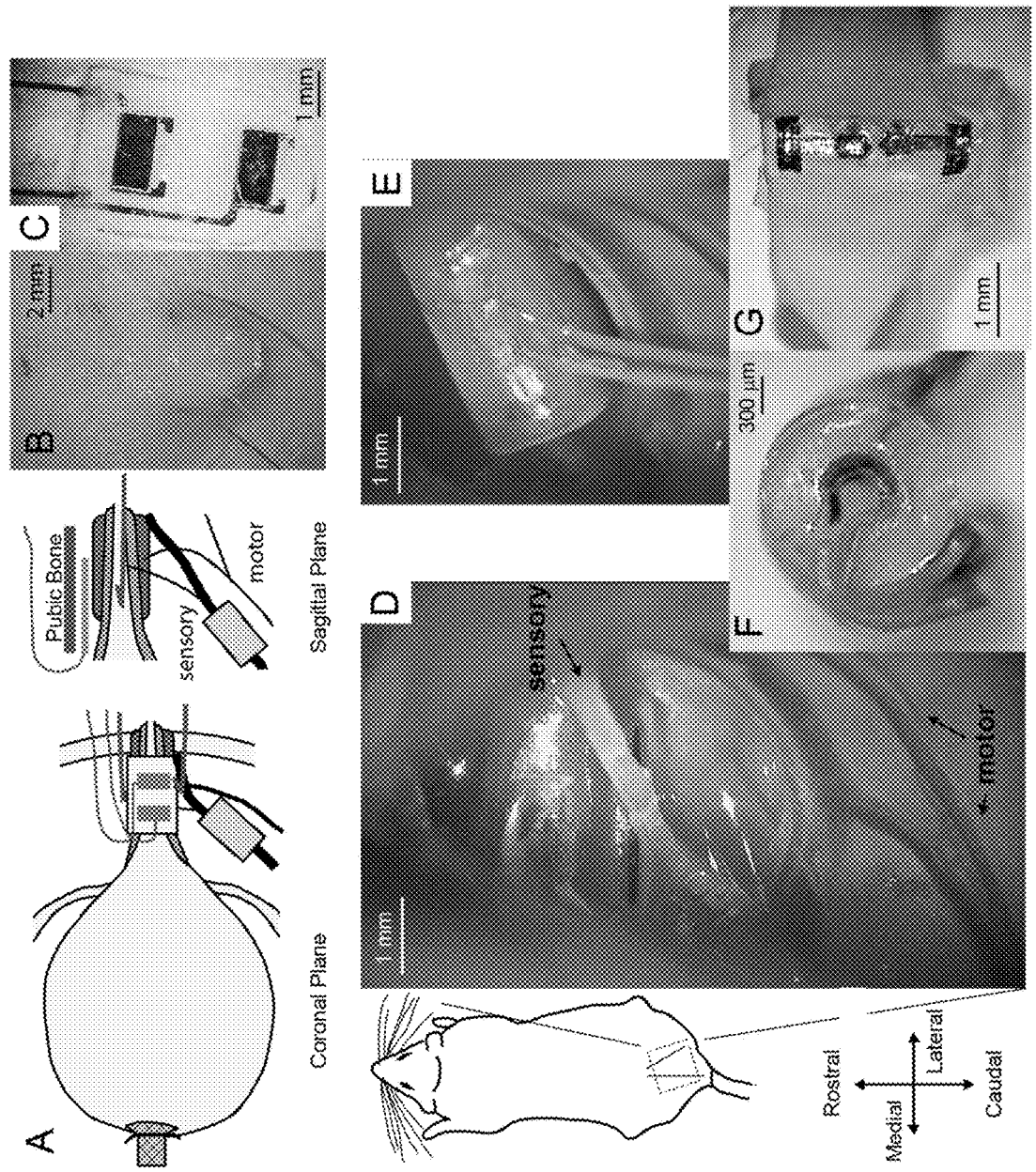
FIG. 2—Experimental Setup (A) Placement of the bladder catheter, nerve cuff, and electrodes for recording external urethral sphincter (EUS) electromyogram (EMG). Two different types of EMG electrodes were used (in different experiments), percutaneous wires (B) and flat metal contacts embedded in a silicone substrate (C) that was placed underneath the pubic bone. (D) View through the surgical microscope of the isolated sensory pudendal nerve in the ischiorectal fossa. (E) View showing placement of the nerve cuff on the sensory pudendal nerve. (F) Side view of a nerve cuff showing the orientation of the incoming wires, as well as the tabs that are used to open the cuff. (G) View of the inside of the nerve cuff after pulling the cuff open at the tabs. The exposed portion of the contacts are near the outside of the cuff.

External urethral sphincter (EUS) EMG was measured using two different approaches (FIG. 2A). Experiments with Prostaglandin E2 (PGE2) used two PFA-coated platinum-iridium wires (140 μm diameter, A-M Systems, Sequim, Wash.). These wires were inserted percutaneously using a needle to pierce the skin, one on each side of the urinary meatus (FIG. 2B). Saline-only experiments used two platinum contacts bonded to a silicone backing with wires welded to each contact (FIG. 2C). This sheet-electrode was placed between the urethra and the pubic symphysis using an intra-abdominal approach. EUS EMG leads were connected through a preamplifier (HIP5, Grass Products, Warwick, R.I.) to an amplifier (P511, Grass Products), and a subcutaneous needle served as ground. Signals were filtered (3 Hz-3 kHz) and sampled at 20 kHz.

After placing the bladder catheter and EUS EMG electrodes, the animal was carefully flipped into a prone position. After resecting gluteal muscles at the midline, the ischium was spread apart from the sacrum to expose the ischiorectal fossa, and the sensory branch of the pudendal nerve was isolated from connective tissue (FIG. 2D). For PGE2 experiments custom bipolar nerve cuffs were placed around the sensory branch and held in place with the use of Kwik-Cast (World Precision Instruments, Sarasota, Fla.). The custom cuffs consisted of 10 stranded stainless steel wire (AS631, Cooner Wire Co, Chatsworth, Calif.) placed through 2 mm long, 500 µm inner-diameter, silicone tubing approximately 1 mm apart. The exposed wires were insulated with silicone (MED-1137, NuSil, Carpinteria, Calif.) and a slit was cut along the length of the tubing to allow placement of the nerve into the cuff. For saline-only experiments, the same custom nerve cuff was used in one experiment. For other saline-only experiments nerve cuffs that were 200 µm inner diameter with 2 mm length (n=4) or 300 µm inner diameter with 3 mm length (n=4) (FIG. 2F,G) (CorTec, Freiburg, Germany) were used. Following nerve cuff placement the opening was sutured closed in layers with 3-0 silk suture. The animal was then carefully flipped back into a supine position for cystometric testing.

Preliminary testing indicated that 100 µM PGE2 consistently reduced bladder capacity as a model of OAB. PGE2 (Sigma-Aldrich) was dissolved in ethanol to 10 mM concentration and stored in a −20° C. Freezer. On days of experiments, this stock solution was diluted in saline to the desired concentration.

Experimental Procedures

The stimulus amplitude required to evoke a reflex response in the external urethral sphincter (EUS) was determined. With the bladder empty, stimuli were delivered at 0.1 to 1 Hz to the sensory pudendal nerve while monitoring evoked EUS EMG activity on an oscilloscope. The amplitude required to evoke consistently (more than 50% of the time) reflex activation of the EUS was considered the stimulus threshold or 1 T (1 times threshold) and was verified to within 10% accuracy. Experiments with percutaneous EMG electrodes (PGE2 experiments) did not show consistent reflex activation of the sphincter. In these experiments a 200 µA stimulus was used primarily (n=6), based on some preliminary testing with intravesical saline.

Figure 4:
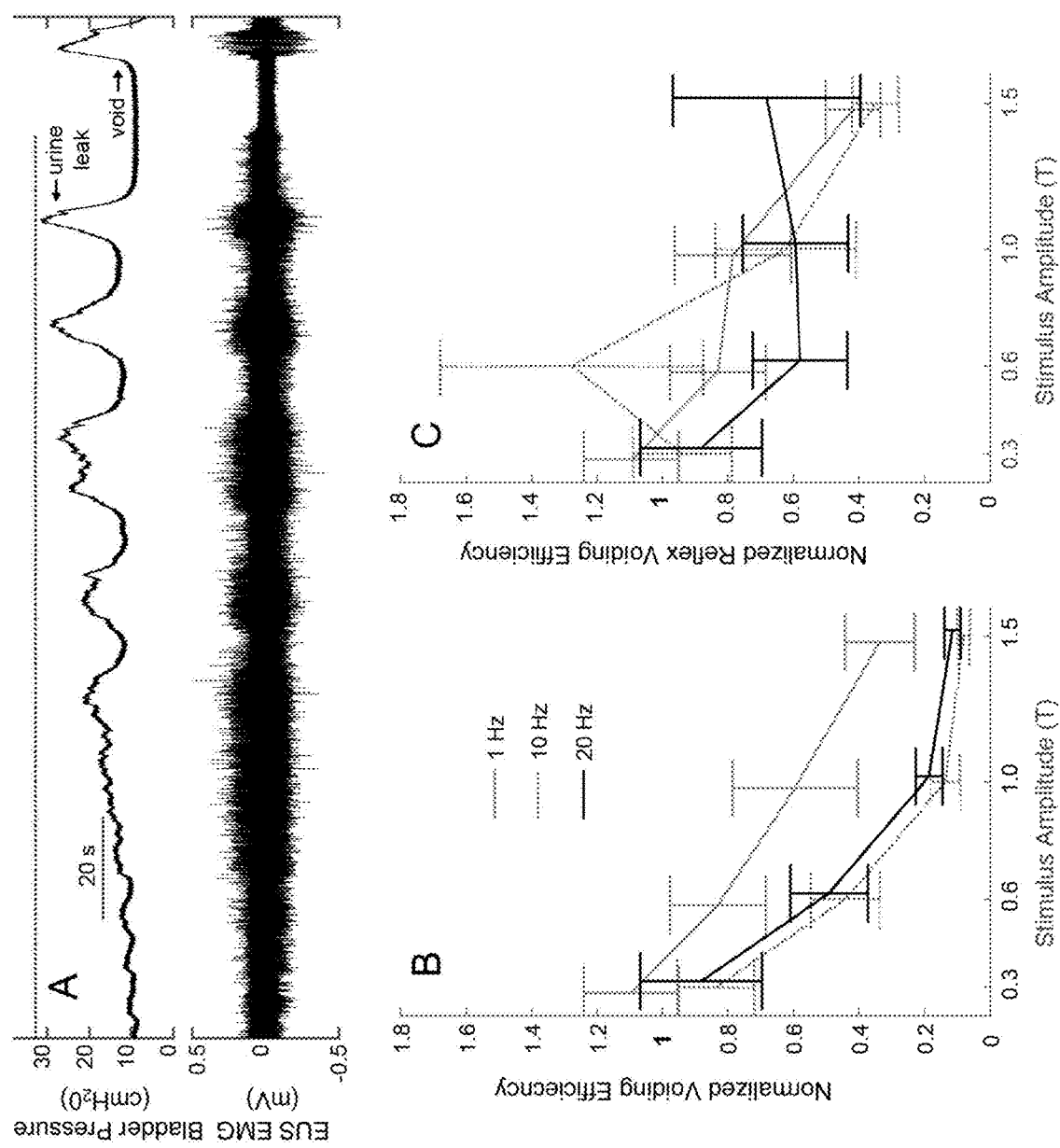
FIG. 4: Impact of sensory pudendal nerve stimulation on voiding efficiency (A) Portion of a trial with stimulation at 1.5 T, 20 Hz illustrating stimulus termination following the first expulsion of urine. The expelled urine was collected and measured. If a second void occurred within twenty seconds of stimulus termination the urine was collected separately and measured (n=7 experiments). The volume from the first micturition event contributed to the normalized voiding efficiency. Values were normalized relative to non-stimulation control trials. Volumes from both the first micturition event and the second micturition event (if present) contributed to the normalized "reflex" voiding efficiency. (B) Summary data showing changes in voiding efficiency, relative to non-stimulation control trials, as a function of stimulus amplitude and repetition frequency (mean±standard error). Voiding efficiency varied as a function of amplitude and frequency (p<0.001 for both amplitude and rate, two-way ANOVA) with no statistically significant interaction term (n=7 for 0.3 T to 1 T, n=6 for 1.5 T, 20 Hz, and n=5 for 1.5 T, 1 and 10 Hz). Increasing stimulation amplitude decreased normalized voiding efficiency. This decrease was larger at 10 and 20 Hz than 1 Hz (C) Waiting up to 20 seconds following stimulus termination elicited subsequent bladder contractions that resulted in the expulsion of additional fluid. Despite the increase in expelled fluid, voiding efficiency remained reduced for 1 Hz (p=0.002) and 10 Hz (p<0.001) at 1.5 T (the amplitude which led to the greatest increase in bladder capacity). Statistical tests versus controls consisted of t-tests comparing distributions to a mean of 1.

The bladder was filled continuously with physiological saline at room temperature (2-8 ml/hr) using an infusion pump with an open urethra for at least 45 minutes during post-surgical recovery. The bladder was subsequently emptied and cystometrograms (CMGs) recorded. For each CMG, the bladder was filled until a micturition event was observed, at which time the infusion pump was turned off. For PGE2 experiments, approximately one minute after the bladder pressure returned to baseline, the bladder was emptied via the catheter using a syringe. For non-stimulated trials in saline-only experiments the bladder was emptied immediately following bladder pressure return to baseline. For stimulation in saline-only experiments, two approaches were used. In the first two experiments, the bladder was emptied upon pressure return to baseline, the same as during non-stimulated trials. In the last seven experiments, the stimulus was terminated following the first micturition event, and if after approximately 20 seconds no micturition event had occurred, then the bladder was emptied. However, if another micturition event occurred, the bladder was emptied after the bladder pressure returned to baseline (FIG. 4A). Voided and residual volumes were recorded and used to calculate bladder capacity and voiding efficiency. For saline-only experiments in which a second micturition event occurred before bladder emptying, the voided volume from the first and second micturition events were collected separately. For these trials, voiding efficiency was calculated as the first voided volume divided by the bladder capacity, and "reflex" voiding efficiency was calculated as the sum of the two voided volumes divided by the bladder capacity.

For PGE2 experiments, following control CMGs with saline the bladder was infused continuously with 100 µM PGE2 solution for 1 hour. The bladder was subsequently emptied, and CMGs recorded while filling the bladder with 100 µM PGE2. Following baseline PGE2 trials, trials with sensory pudendal stimulation were interleaved with PGE2 trials without stimulation.

Figure 5:
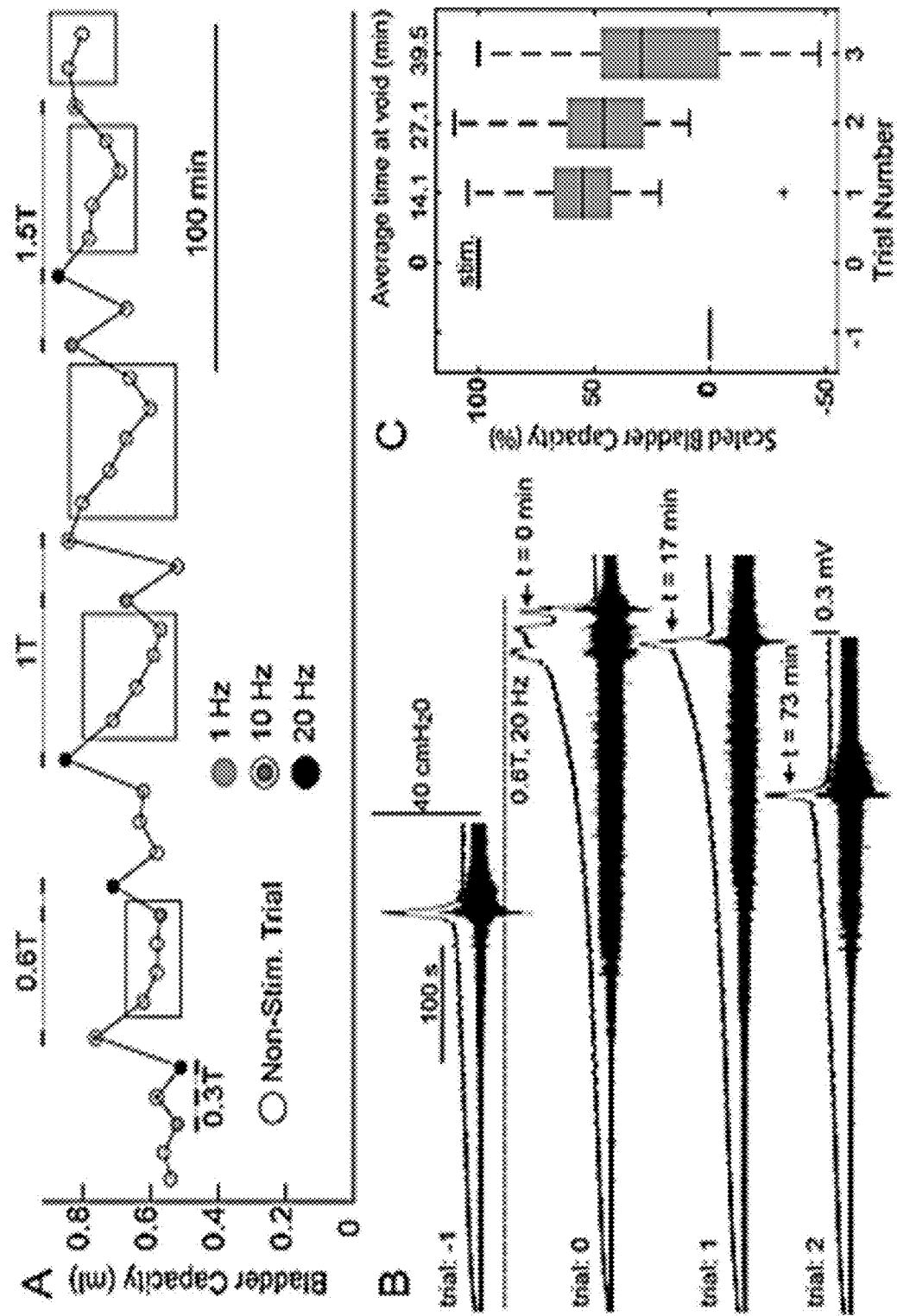
FIG. 5: Stimulation of the sensory pudendal nerve leads to increases in bladder capacity (stimulation carryover effect)

For saline-only experiments, sensory pudendal stimulation trials followed baseline control trials. Following trials in which stimulation increased bladder capacity (approximately greater than 20%), non-stimulation trials were run until the bladder capacity returned to a steady-state (FIG. 5A). Stimulation amplitudes (0.3 T, 0.6 T, and 1 T, n=9, and 1.5 T, n=6 for 1 Hz, 10 Hz and n=7 for 20 Hz) were tested from lowest to highest due to concerns of higher-amplitude stimuli producing lasting changes in bladder capacity. At each amplitude three stimulus rates were presented (1, 10, and 20 Hz) in randomized order. Stimuli were biphasic, 100 µs per phase pulses delivered via a voltage to current convertor (Model 2200, A-M Systems) controlled via an analog output channel on the PowerLab system. Electrical stimulation started at the start of the pump and stopped at the first micturition event (n=9, PGE2 and n=7, saline-only) or went throughout the entire trial (n=2, saline-only).

For PGE2 experiments, stimulation testing started at 100 µA (n=1), 200 µA (n=6), or 400 µA (n=2), all at 20 Hz. In cases where the stimulation did not clearly increase bladder capacity (n=2), the stimulus amplitude was increased by a factor of two until an increase in bladder capacity was evident. In one experiment this occurred after one increase (2×), and in the other experiment two increases were necessary (4× initial amplitude).

Data Analysis

All signals were collected using a PowerLab/16SP acquisition unit (AD Instruments, Colorado Springs, Colo.) in conjunction with Labchart Pro for visualization (Versions 7 & 8, AD Instruments). All analysis was performed using Matlab (Mathworks, Natick, Mass.). Bladder capacity was calculated as the sum of the residual and voided volumes. Voiding efficiency was calculated as the voided volume divided by the bladder capacity. For saline-only experiments in which two voids were allowed, the output from both voids was summed to create a secondary measure of voiding efficiency (reflex voiding efficiency).

For display, pressure traces were low-pass filtered using a first-order zero-phase Butterworth filter with a 5 Hz cutoff. EUS EMG was high pass filtered at 70 Hz using a first-order zero-phase Butterworth filter.

Summary data are presented as either mean±standard error or as boxplots using Matlab's boxplot( ) function. All repeated trials within an experiment were averaged together to create a single value per experiment. Voiding efficiency and bladder capacity values were normalized to non-stimulation saline control trials. For saline-only experiments, the normalization was made relative to non-stimulation trial data captured prior to any stimulation. Normalized data were included in two-way ANOVA analysis (anovan( ), Matlab). Paired t-tests were used for comparison of different conditions, with the exception of comparison to control values where a t-test compared whether or not a condition's mean was different than 1(ttest(x,y) and ttest(x,1), Matlab). Tests with $p \leq 0.05$ were considered to be statistically significant.

Figure 3:
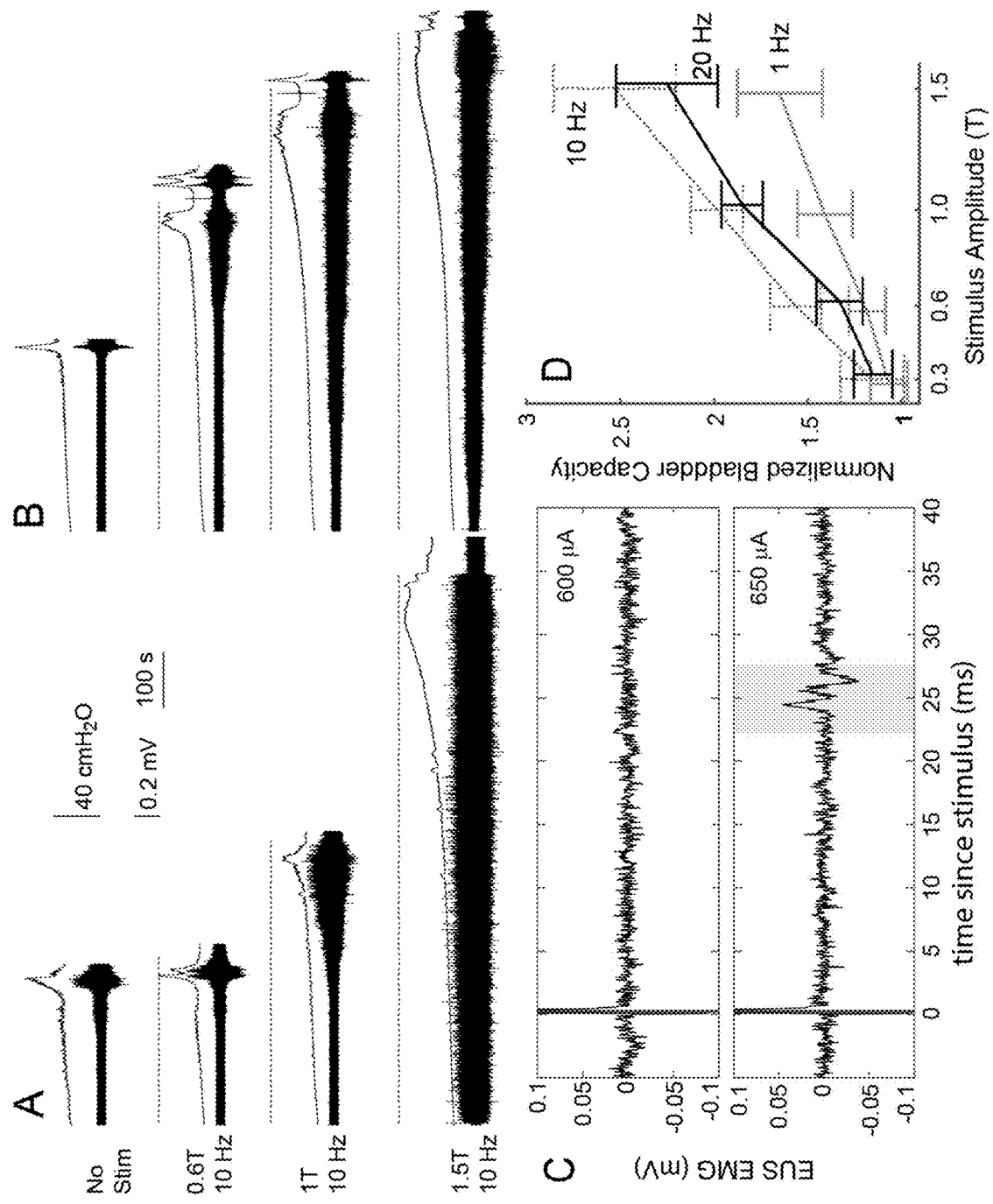
FIG. 3—Sensory pudendal nerve stimulation increased bladder capacity (A)(B) Example traces from two experiments showing increases in bladder capacity with increasing stimulation amplitude at 10 Hz. Traces are bladder pressure and EUS EMG. Dotted lines above the pressure traces indicate periods of stimulation. (C) Reflex EMG responses to stimulus at amplitudes of 600 and 650 µA. A reflex response at 25 ms is present at 650 µA, but not at 600 µA. Other amplitudes are reported as fractions of the stimulus reflex threshold (or 1 T). (D) Summary data showing changes in bladder capacity, relative to non-stimulation control trials, as a function of stimulus amplitude and repetition frequency (mean±standard error). Bladder capacity varied as a function of amplitude and frequency ($p<0.001$ for both amplitude and rate, two-way ANOVA) with no statistically significant interaction term (n=9 for 0.3 T to 1 T, n=7 for 1.5 T, 20 Hz, and n=6 for 1.5 T, 1 and 10 Hz). Increasing stimulus amplitude led to increased bladder capacities. Statistically significant increases from 1 T to 1.5 T stimulation were observed for 1 and 20 Hz (p=0.01 and p=0.03, paired t-tests), but not for 10 Hz. The average normalized bladder capacity during 10 Hz stimulation was greater than during 20 Hz stimulation only at 0.6 T ($p<0.001$).

Example 1—Effect of Sensory Pudendal Nerve Stimulation During Single-Fill Cystometry on Bladder Capacity In order to assess the possible use of pudendal nerve stimulation in the treatment of OAB, bladder capacity following pudendal nerve stimulation was assessed in female Wistar rats. Here bladder capacity was shown to increase following pudendal nerve stimulation (FIG. 3).

The increase in bladder capacity was dependent upon stimulation amplitude and repetition frequency (two-way ANOVA, $p<0.001$ for both amplitude and frequency, n=9 for 0.3 T to 1 T, n=7 for 1.5 T, 20 Hz, and n=6 for 1.5 T, 1 and 10 Hz). The largest increase was at 1.5 T at 10 Hz, in which the average bladder capacity was 253% of the non-stimulated control trials. Stimulation at 10 Hz led to the largest increases in bladder capacity, but the relative increases in bladder capacity were not different between 10 and 20 Hz except at 0.6 T ($p<0.001$) (FIG. 3D). Increasing stimulation amplitude from 1 T to 1.5 T resulted in an increase in bladder capacity for 1 Hz and 20 Hz stimulation ($p=0.01$ and $p=0.03$ respectively), but not for 10 Hz.

There was evidence of saturation at 10 Hz, as the increase in bladder capacity was not statistically different between 1 T and 1.5 T. This was dependent on the experiment, as can be seen by the differences in bladder capacity between 1 T and 1.5 T in FIG. 3A and FIG. 3B.

Example 2—Effect of Sensory Pudendal Nerve Stimulation During Single-Fill Cystometry on Voiding Efficiency Further tests were performed in order to determine the effect of sensory pudendal nerve stimulation on voiding efficacy.

Increasing stimulation amplitude also led to a decrease in voiding efficiency. Changes in voiding efficiency were also dependent upon stimulation amplitude and repetition frequency (two-way ANOVA, $p<0.001$ for both amplitude and frequency, n=7 for 0.3 T to 1 T, n=6 for 1.5 T, 20 Hz, and n=5 for 1.5 T, 1 and 10 Hz) (FIG. 4B). On average 10 Hz stimulation led to the largest decreases in voiding efficiency. At higher amplitudes, micturition events followed termination of the stimulus. However, at the amplitude which yielded the largest increases in bladder capacity, "reflex" voiding efficiency was still less than control values for 1 or 10 Hz ($p=0.002$ and $p<0.001$ respectively). The reflex voiding efficiency was not statistically different from control values for 1.5 T, 20 Hz.

At the highest stimulation amplitudes tested, it was not uncommon for small amounts of leaking to occur at high bladder pressures, rather than a coordinated contraction. Termination of the stimulus allowed subsequent voids to occur, but voiding efficiency was still reduced relative to non-stimulated trials.

Example 3—Effect of Sensory Pudendal Nerve Stimulation During Single-Fill Cystometry on Subsequent Non-Stimulated Trials In order to determine whether the therapeutic effect of sensory pudendal nerve stimulation could provide an ongoing treatment for OAB once nerve stimulation had been halted, the effect of sensory pudendal nerve stimulation during single-fill cystometry on subsequent non-stimulated trials was investigated.

Stimulation of the sensory pudendal nerve often produced a carry-over effect and bladder capacity was increased on subsequent non-stimulation trials (FIG. 5A, B). Due to high variability in the magnitude of this effect, bladder capacity values from trials that followed 1 or 1.5 T and 10 or 20 Hz were combined in summary data (FIG. 5C). Only groups of trials in which stimulation increased bladder capacity by at least 20% relative to the preceding control trial and in which at least three non-stimulated trials followed the stimulated trial were included (n=15, 48% of trials). For the first trial following a stimulation trial, bladder capacity remained elevated by 55% (median) relative to baseline. For the third non-stimulation trial, with a void at an average of 39.5 minutes following termination of the stimulus, the bladder capacity remained elevated by 29%.

The time to return back to a steady-state bladder capacity varied, but tended to occur within 1 hour. The utility of this observation is unclear, especially given that the maximum level of inhibition (maximum bladder capacity) occurred during stimulation, not after, but it may suggest that intermittent stimulation will be sufficient to treat the symptoms of OAB.

Example 4—Effect of Intravesical PGE2 on Bladder Capacity and Voiding Efficiency Intravesical PGE2 reduces bladder capacity in rats (Ishizuka et al. 1995) and causes "a strong urgency sensation" when given to healthy women, also leading to reduced bladder capacities (Schussler et al. 1990). Consistent with these observations, intravesical PGE2 reduced bladder capacity.

Intravesical PGE2 decreased bladder capacity ($p=0.02$) and increased voiding efficiency ($p<0.001$, n=9) (FIG. 6). Sensory pudendal nerve stimulation at 20 Hz increased bladder capacity relative to PGE2 ($p=0.004$). Similar to the results with saline, an increase in bladder capacity from stimulation also resulted in a decrease in voiding efficiency relative to the PGE2 condition. These preliminary results provide evidence that sensory pudendal nerve stimulation may work under a variety of conditions.

All PGE2 experiments were conducted prior to saline-only experiments. The impact of intravesical PGE2 on bladder capacity appeared to change over time. By comparison, intravesical saline-only appeared to be much more stable (consistent bladder capacity over time). Coupled with the unexpected presence of stimulation carryover effects which meant single testing blocks could take 2-3 hours, saline-only was judged to be more well-suited for initial exploration of the stimulus parameter space.

Sensory pudendal nerve stimulation increased bladder capacity in the anesthetized female Wistar rat during intravesical saline and PGE2 conditions. 10 Hz stimulation at 1.5 T led to the largest increase in bladder capacity. Stimulation that produced increases in bladder capacity also led to decreases in voiding efficiency.

Example 5—Effects of State-Dependent Pudendal Nerve Stimulation

In order to evaluate the effect of stimulating the pudendal nerve during different phases of the micturition cycle—also referred to as "state-dependent stimulation"—three experiments were conducted in alpha-chloralose anesthetized male cats.

Nerve cuff electrodes were placed on the sensory and motor branches of the pudendal nerve, just distal to the branching of the compound pudendal nerve (pudendal sensory branch used was the dorsal nerve of the penis (DNP)). Stimulation and control trials were interleaved with random within-block ordering.

In experiment 1, unstimulated controls (FIG. 7, trace A) were compared to 3 stimulation regimes (FIG. 7, traces B-D). Stimulation (shown by dashed line below each trace) consisted of the stimulus during bladder filling (3 T, 10 Hz), followed by either: B) the same stimulus during voiding (state independent); C) a termination of the stimulus at void onset, D) switching the stimulation rate to 33 Hz at void onset. In a second and third experiment, a fourth stimulation regime (E) was also used (FIGS. 8 and 9). In this regime, DNP stimulation was terminated at void onset and motor branch stimulation starting during voiding. The stimulation pattern used during motor branch stimulation consisted of stimulus trains at 40 Hz lasting for 100 ms in duration, repeated at 2 Hz. Amplitudes of 1.8-2.3 T were selected as they maximized evoked external anal sphincter EMG. Approaches C-E are referred to as state-dependent stimulation, as the stimulus parameters used depend on the state of the subject—i.e. whether bladder filling or bladder voiding is occurring.

Average bladder capacity and voiding efficiency values are from 2-3 cystometric trials.

Results

By using state-dependent stimulation it is shown it is possible to not only increase bladder capacity beyond the no-stimulation condition, but that voiding efficiency can be increased to higher levels than those observed during state-independent stimulation.

In the first experiment, stimulation of the DNP throughout an entire cystometric trial (filling and voiding) increased bladder capacity (FIG. 7B) relative to no-stimulation (FIG. 7A). By terminating the stimulus or increasing the frequency of the stimulus signal at void onset voiding efficiency increased even further than when stimulation occurred throughout the trial (state-dependent stimulation, FIG. 7C, D).

Similar results were obtained in the second experiment (FIG. 8). In addition to the previously tested approaches to state-dependent stimulation, the motor "bursting" pattern was tested during voiding (FIG. 8E) which led to increased voiding efficiency (50.8 ml, 83%, FIG. 8E). In the third experiment, the baseline bladder capacity (no-stimulation condition) was elevated (compared to the other two experiments). Stimulation increased the bladder capacity, but only slightly (7% increase). In this experiment state-dependent stimulation with motor bursting led to both an increase in bladder capacity and voiding efficiency (FIG. 9E).

In three experiments state-dependent stimulation increased bladder capacity relative to controls and voiding efficiency relative to state-independent stimulation. In all experiments, stimulation of the sensory pudendal nerve increased bladder capacity. In two out of three experiments state-dependent stimulation using stimulus termination or switching to higher frequency stimulation at onset of voiding led to increased voiding efficiency. In two experiments state-dependent stimulation using motor branch burst stimulation during voiding increased voiding efficiency.

II. Experimental Dataset 2

The following experimental methods were used throughout Examples 6-8 discussed below.

Rat Surgical Preparation and Procedures

Female Wistar rats (n=25) weighing between 237 and 296 g were anesthetized with urethane (1.2 g/kg SC, supplemented as necessary). Body temperature was monitored using an esophageal temperature probe and maintained at 36-38° C. with a water blanket. Heart rate and arterial blood oxygen saturation levels were monitored using a pulse oximeter (Nonin Medical Inc., 2500A VET).

In preparation for cystometrogram (CMG) measurements, the bladder was exposed via a midline abdominal incision. The tip of a polyethylene (PE-90) catheter (Clay Adams, Parsippany, N.J) was heated to create a collar and inserted into the bladder lumen through a small incision in the apex of the bladder dome which was secured with a 6-0 silk suture. The abdominal wall was closed in layers with 3-0 silk suture. The bladder catheter was connected via a 3-way stopcock to an infusion pump (Braintree Scientific Inc., BS-8000 or Harvard Apparatus PHD 4400) and to a pressure transducer (ArgoTrans, ArgonMedical Devices Inc., Plano, Tex.) connected to a bridge amplifier and filter (13-6615-50, Gould Instruments, Valley View, Ohio) for measuring intravesical pressure (IVP). Data were sampled at 1 kHz using a PowerLab system (AD Instruments, Colorado Springs, Colo.).

External urethral sphincter (EUS) EMG was measured using two platinum contacts bonded to a silicone backing with wires welded to each contact (Microleads, Boston). This sheet-electrode was placed intra-abdominally between the urethra and the pubic symphysis. (Hokanson et al., 2017b). EUS EMG leads were connected through a preamplifier (HIP5, Grass Products, Warwick, R.I.) to an amplifier (P511, Grass Products). A subcutaneous needle served as ground. Signals were filtered (3 Hz-3 kHz) and sampled at 20 kHz.

After placing the bladder catheter and EUS EMG electrodes, the animal was turned to a prone position for cuff placement. After resecting gluteal muscles at the midline, the ischium was spread apart from the sacrum to expose the ischiorectal fossa, and the sensory branch of the pudendal nerve was isolated from connective tissue. A custom nerve cuff was used in one experiment. In other experiments either a 300 μm inner diameter with 3 mm length (n=6) or 200 μm inner diameter (2 mm length, n=18) were used (CorTec, Freiburg, Germany). In experiments with motor branch stimulation, the ischiorectal fossa on the opposite side of the animal was exposed and the pudendal motor nerve and blood vessels were isolated. Due to the small size of the motor nerve branch, a 400 μm inner diameter cuff was placed around the pudendal motor branch as well as the pudendal blood vessels (CorTec, n=9). Following nerve cuff placement, the incision was sutured closed in layers with 3-0 silk suture. The animal was then turned back into a supine position for cystometric testing.

The gross neural anatomy of the lower urinary tract in the rat is shown in FIG. 10A. The left inset shows this anatomy relative to the pelvic bones and spinal column. The area highlighted in the inset corresponds to our access point, in the ischiorectal fossa. A picture of the dissection of the sensory nerve branch is shown in FIG. 10B, with a 300 μm inner diameter, 3 mm length positioned close to, but not yet around, the nerve. The type of cuff used in these experiments is shown in FIGS. 10D and 10E. The cuff is inserted around the nerve by pulling on two tabs which open the cuff. Releasing the tabs closes the cuff.

Rat Electrical Stimulation

Electrical stimulation was delivered using a stimulus isolator (n=18) or a stimulus generator (n=7, model STG4002-16 mA, Multi-Channel Systems, Reutlingen, Germany). Stimulation pulses consisted of a charge-balanced biphasic waveform with 100 µs pulse widths. Strength of stimulation was assessed by monitoring evoked EUS EMG. Amplitudes for sensory pudendal nerve stimulation were normalized to the minimum stimulation amplitude necessary to reflexively evoke EUS EMG activity. This stimulation amplitude is referred to as 1 T (1 times threshold amplitude). Motor branch stimulation occurred at the minimum stimulus amplitude required to evoke a maximal (direct) EUS EMG response.

Electrical stimulation to promote bladder filling started at the onset of bladder filling. For one set of animals (n=11), the inhibitory pattern consisted of stimulation at either 1, 10 or 20 Hz and at stimulation amplitudes of 0.3, 0.6, 1, and 1.5 T. In these experiments stimulation persisted throughout the first bladder contraction which led to leakage or a void. An additional one minute worth of data was collected to see termination of the stimulus led to a reflexive void which increased the voiding efficiency back to or above control values. In a second set of experiments (n=9) exploring state-dependent stimulation, stimulation occurred at 10 Hz and 1 T. Depending on the type of trial, stimulation either continued throughout bladder emptying or terminated just prior to bladder emptying. All stimulation to promote bladder filling occurred on the sensory pudendal nerve.

Electrical stimulation to promote bladder emptying started just prior to bladder voiding or urine leakage and continued throughout the bladder contraction. In the first set of state-dependent stimulation experiments (n=9), four approaches to promoting bladder emptying were employed. For the first approach no stimulation occurred, but rather the inhibitory stimulus was terminated such that no stimulation was occurring during bladder emptying. The other three approaches, two of which are shown in FIG. 10F, consisted of three pulses at 40 Hz repeated at either 2 Hz (every 0.5 seconds), 4.76 Hz (every 0.21 seconds), or 8 Hz (every 0.125 seconds). These stimulation patterns were all delivered on the motor branch and we refer to these patterns as motor "bursting" patterns.

Cat Surgical Preparation and Procedures

Acute experiments were conducted in adult neurologically intact male (n=6, 3.4-3.8 kg) and female (n=5, 2.8-3.2) cats. Anesthesia was induced with isoflurane (3%) and maintained with α-chloralose (65 mg/kg initial dose followed by continuous infusion of 5 mg/kg/h iv and supplemented as necessary based on jaw tone and blood pressure) following completion of the surgery. Gentamicin 5 mg IM and ketofen 1.2 g/kg SQ were given prior to surgical incision. A tracheotomy was performed to place a silicone endotube (Cat. no J0612B, Jorgensen Laboratories, Loveland, Colo.) connected to an artificial respirator (ADS 1000, Engler Engineering Corporation, Hialeah, Fla.), and artificial respiration was controlled to maintain end-tidal $CO_2$ between 3-4% (Capnogaurd, Novametrix Medical Systems Inc., Wallingford, Conn.). The right carotid artery was cannulated with a 3.5 Fr polypropylene catheter (Cat. no 8890703211, Medtronic, Minneapolis, Minn.) to monitor arterial blood pressure (Tektronix 413A Neonatal Monitor) and was kept patent by infusing saline at a constant rate of 6 ml/hr. Body temperature was measured using an esophageal temperature probe and maintained at 38° C. with a forced-air warming blanket (Bair Hugger model 505, 3M). Additional fluids (0.9% physiological saline with 5% dextrose and 8.4 g/L $NaHCO_3$) were administered continuously (15 ml/kg/hr, i.v.) via the left cephalic catheter. Following a midline abdominal incision, the bladder was cannulated through the dome with a modified 14 g BD Angiocath catheter connected to PE 90 tubing introduced with a hypodermic needle, secured with a purse string suture (4-0 silk, Cat. No M-S418R19, AD Surgical, Sunnyvale, Calif.) and connected to a solid-state pressure transducer (Deltran, Utah Medical, UT) to measure bladder pressure. A force transducer (model: MLT500D, AD Instruments, Colorado Springs, Colo.) was used to collect voided volume (VV). The external anal sphincter (EAS) EMG activity was measured by PFA-coated platinum-iridium wires (0.0055 inch-diameter, A-M Systems, Sequim, Wash.) inserted percutaneously into the EAS bilaterally. EAS EMG leads were connected through a preamplifier (HIP5, Grass Products, Warwick, R.I.) to an amplifier (P511, Grass Products). Bladder pressure (BP), VV, and EAS EMG signals were amplified, filtered, and sampled at either 1,000 Hz (BP and VV) or 20,000 Hz (EAS EMG).

The bladder was continuously filled with physiological saline at room temperature (0.2-4 ml/min, median=1.3 ml/min) using an infusion pump (model: PHD 4400, Harvard Apparatus), with an open urethra for approximately one hour to allow post-surgical recovery. The bladder was subsequently emptied and cystometrograms (CMGs) recorded. For each CMG, the bladder was filled micturition or urine leakage occurred until, at which time the infusion pump was turned off. Approximately one minute after the bladder pressure returned to baseline, the bladder was emptied via the catheter using a syringe. Within a block of trials, the filling rate remained constant. Voided (VV) and residual (RV) volumes were recorded and used to calculate bladder capacity (BC) and voiding efficiency (VE).

Cat Electrical Stimulation

Electrical stimulation was delivered using a stimulus generator (model STG4002-16 mA, n=4 and model STG4004-16 mA, n=7, Multi-Channel Systems). Stimulation pulses consisted of a charge-balanced biphasic waveform with 100 µs per phase. Strength of stimulation was assessed by monitoring evoked EAS EMG. For sensory pudendal stimulation (females) and dorsal genital nerve stimulation (males), stimulus threshold was defined as the stimulus amplitude necessary to evoke reflex EAS EMG activity. For motor branch (i.e. rectal-perineal nerve) nerve stimulation, the minimum amplitude that evoked a maximal EAS EMG response was used.

Electrical stimulation to promote bladder filling started at filling onset. The stimulus consisted of sensory pudendal nerve (female) or dorsal genital nerve (males) stimulation at 3 T and 10 Hz. In some trials this stimulation persisted throughout a voiding contraction.

In other trials state-dependent stimulation was employed in an attempt to increase voiding efficiency. One approach for state-dependent stimulation was to terminate the stimulus at void onset. A second approach was to change the stimulation rate on the sensory pudendal or dorsal genital nerves from 10 Hz to 33 Hz at void onset. The third approach was to employ a bursting pattern at void onset. All bursting patterns consisted of 3 pulses at 40 Hz at a 2 Hz train rate. Unlike the rat experiments the train rate was not changed. For motor stimulation, this bursting occurred at the minimum stimulus amplitude which generated the maximal EAS EMG response. For sensory pudendal or dorsal genital nerve stimulation this occurred at 3 T, the same amplitude used for 10 Hz stimulation during bladder filling.

Data Analysis

For each trial (cystometrogram) bladder capacity was calculated as the sum of the voided volume and the residual volume extracted from the bladder. Voiding efficiency was calculated as the ratio of the voided volume to the bladder capacity.

Stimulus patterns were randomized within block and values were normalized to preceding control levels for plotting and summary statistics (e.g. median values). For state-dependent stimulation data voiding efficiency was compared between no-stimulation controls, continuous stimulation, and the state-dependent stimulation conditions. This was done by use of Friedman ANOVA test, followed by the Benjamini, Krieger and Yekutieli two-stage step-up method for post-hoc comparison of conditions to continuous stimulation. This ANOVA test requires no missing data for any stimulus condition, so the number of complete data sets was reduced to five for both state-dependent stimulation in male cats and female rats. The ANOVA and post-hoc testing were computed using GraphPad (Version 7.04, La Jolla, Calif.).

Example 6—Impact of Continuous Sensory Pudendal Stimulation on Bladder Capacity as a Function of Stimulation Amplitude and Pulse Repetition Rate In female rats (n=9) the impact of continuous sensory pudendal stimulation on bladder capacity was evaluated as function of stimulation amplitude and pulse repetition rate. Example cystometrograms from one animal are shown in FIG. 11A. Stimulation continued until urine was lost either through leakage or voiding contraction. Increasing stimulation amplitude increased bladder capacity and the increase in bladder capacity was dependent on stimulation rate (FIG. 11B). The largest increases in bladder capacity came from stimulation at 1.5 T, with average normalized bladder capacities of 1.65 (1 Hz), 2.53 (10 Hz), and 2.25 (20 Hz) of control values. In addition to increasing bladder capacity, increasing stimulation amplitude also decreased voiding efficiency. This can also be seen in the pressure traces (FIG. 11A) where increasing stimulation amplitude led to slow rises in bladder pressure towards the end of filling, rather than coordinated contractions.

Example 7—Continuous Stimulation of the Dorsal Genital Nerve (DGN) and State-Dependent Stimulation in Male Cats FIG. 12 shows the results of experiments using continuous stimulation of the dorsal genital nerve (DGN) and state-dependent stimulation as tested in male cats (n=6). In this example continuous stimulation decreased voiding efficiency by 24%. Across all experiments continuous stimulation decreased voiding efficiency by 33% (median) relative to controls (FIG. 12C), confirming the results from experiments in rats, although this trend was not statistically significant (p=0.072, n=5).

Bladder capacity results were combined across all stimulation trials as stimulation during bladder filling was identical in all trials up until void onset and stopping of the infusion pump. All experiments showed increased bladder capacity from DGN stimulation with a median increase of 26% relative to the no-stimulation condition (FIG. 12B).

Both termination of continence-promoting inhibitory stimulation at the onset of voiding, and 33 Hz stimulation during voiding on average increased voiding efficiency relative to control voiding efficiency with no inhibitory stimulation (14% and 19% medians respectively), although neither was statistically significant (p>0.05, n=5). The largest and most consistent increase in VE came from switching to burst stimulation of the motor pudendal nerve branch, which produced a 379% median increase in VE (p=0.028). Relative to continuous stimulation, state-dependent stimulation led to statistically-significant increases in voiding efficiency (p=0.003 for ANOVA test, p=0.028 for fill only, p=0.048 for 33 Hz, p<0.001 for motor bursting, n=5) (data shown in FIG. 12C includes n=5 for motor bursting, n=6 for others).

Similar data was collected in female cats (n=5). Example traces from an experiment are shown in FIG. 14A. Continuous stimulation increased bladder capacity but decreased voiding efficiency by 52%. Side-by-side male and female cat summary data is shown in in FIGS. 14B and 14C. State-dependent stimulation increased bladder capacity in males by 26% (median, n=6 males) and in females 15% (median, n=5) relative to control trials. In female cats continuous stimulation decreased voiding efficiency (median 21% decrease). Unlike in male cats, fill-only and 33 Hz stimulation conditions yielded voiding efficiencies that are on average less than controls (42% and 50% decreases respectively relative to controls) in female cats. Similar to male cats, state-dependent stimulation in female cats with motor bursting increased bladder capacity and voiding efficiency (median 100% increase) relative to the control condition. Interestingly, in all experiments, motor bursting increased voiding efficiency relative to control trials.

Example 8—State-Dependent Stimulation Using Motor Bursting to Increase Voiding Efficiency in the Rat FIG. 13 shows results of state-dependent stimulation using motor bursting to increase voiding efficiency in the rat. Termination of the stimulus, and in some trials, a transition to motor bursting occurred just prior to the volume at which a bladder contraction was anticipated. As expected and consistent with previous experimental results (FIG. 11), sensory pudendal nerve stimulation increased bladder capacity to 158% (median) of no-stimulation control trials (FIG. 13B, n=9). State dependent stimulation also increased voiding relative to continuous stimulation (data shown in FIG. 13C includes n=5 for 8 Hz bursting, n=8 for 4.76 Hz bursting, n=9 for others) (p=0.023 for ANOVA, p=0.016 for fill-only, p=0.001 for 2 Hz, p=0.003 for 4.76 Hz, p=0.004 for 8 Hz, n=5). Median normalized voiding efficiency values were 19% (continuous stimulation), 48% (fill-only), 98% (2 Hz motor), 117% (4.76 Hz motor), and 75% (8 Hz motor).

REFERENCES

Brindley G S, Rushton D N, Craggs M D. The pressure exerted by the external sphincter of the urethra when its motor nerve fibres are stimulated electrically. *Br J Urol* 46: 453-62, 1974.

Chen M L, Shen B, Wang J, Liu H, Roppolo J R, De Groat W C, Tai C. Influence of naloxone on inhibitory pudendal-to-bladder reflex in cats. *Exp Neurol* 224: 282-91, 2010.

Farag F F, Martens F M J, Rijkhoff N J M, Heesakkers J P F A. Dorsal genital nerve stimulation in patients with detrusor overactivity: A systematic review. *Curr Urol Rep* 13: 385-388, 2012.

Goldman H B, Amundsen C L, Mangel J, Grill J H, Bennett M, Gustafson K J, Grill W M. Dorsal genital nerve stimulation for the treatment of overactive bladder symptoms. *Neurourol Urodyn* 27: 499-503, 2008.

Hokanson J A, Langdale C L, Sridhar A, Grill W M (2017a) Stimulation of the Sensory Pudendal Nerve Increases Bladder Capacity in the Rat. Am J Physiol Renal Physiol: ajprena1003732017.

Hokanson J A, Langdale C L, Sridhar A, Grill W M (2017b) OAB without an overactive bladder in the acute prostaglandin E2 rat model. Am J Physiol Renal Physiol 313: F1169-F1177.

Ishizuka O, Mattiasson A, Andersson K-E. Prostaglandin E2-induced bladder hyperactivity in normal, conscious rats: involvement of tachykinins? *J Urol* 153: 2034-8, 1995.

Langdale C L, Grill W M (2016) Phasic activation of the external urethral sphincter increases voiding efficiency in the rat and the cat. Exp Neurol 285:173-181.

Larson J a, Ogagan P D, Chen G, Shen B, Wang J, Roppolo J R, de Groat W C, Tai C. Involvement of metabotropic glutamate receptor 5 in pudendal inhibition of nociceptive bladder activity in cats. *J Physiol* 589: 5833-43, 2011.

Mangera A, Apostolidis A, Andersson K E, Dasgupta P, Giannantoni A, Roehrborn C, Novara G, Chapple C. An updated systematic review and statistical comparison of standardised mean outcomes for the use of botulinum toxin in the management of lower urinary tract disorders. *Eur Urol* 65: 981-90, 2014.

Martin W D, Fletcher T F, Bradley W E (1974) Innervation of feline perineal musculature. Anat Rec 180:15-29.

Mashni J W, Peters K M. Potential Use of Pudendal Nerve Stimulation for Voiding Dysfunction. *Curr Bladder Dysfunct Rep* 5: 177-182, 2010.

McGee M J, Danziger Z C, Bamford J a, Grill W M. A spinal GABAergic mechanism is necessary for bladder inhibition by pudendal afferent stimulation. *Am J Physiol Renal Physiol* 307: F921-30, 2014.

McKenna K E, Nadelhaft I (1986) The organization of the pudendal nerve in the male and female rat. J Comp Neurol 248:532-549.

Peng C-W, Chen J-J J, Cheng C-L, Grill W M (2008) Improved bladder emptying in urinary retention by electrical stimulation of pudendal afferents. J Neural Eng 5:144-154.

Schüssler B. Comparison of the mode of action of prostaglandin E2 (PGE2) and sulprostone, a PGE2-derivative, on the lower urinary tract in healthy women. A urodynamic study. *Urol Res* 18: 349-52, 1990.

Snellings A E, Grill W M. Effects of stimulation site and stimulation parameters on bladder inhibition by electrical nerve stimulation. *BJU Int* 110: 136-143, 2012.

Su X, Nickles A, Nelson D E. Comparison of neural targets for neuromodulation of bladder micturition reflex in the rat. *Am J Physiol Renal Physiol* 303: F1196-206, 2012.

Wenzel B J, Boggs J W, Gustafson K J, Grill W M (2006) Closed loop electrical control of urinary continence. J Urol 175:1559-1563.

Woock J P, Yoo P B, Grill W M. Activation and inhibition of the micturition reflex by penile afferents in the cat. *Am J Physiol Regul Integr Comp Physiol* 294: R1880-9, 2008.

Yoo P B, Woock J P, Grill W M (2008) Bladder activation by selective stimulation of pudendal nerve afferents in the cat. Exp Neurol 212:218-225.

CLAUSES

The following clauses describe further embodiments of the invention:

Clause 1. An apparatus for stimulating neural activity in a pudendal nerve of a subject, the apparatus comprising:
at least one primary electrode configured to apply a first electrical signal to said nerve; and
a controller coupled to said primary electrode(s) and controlling the first electrical signal to be applied thereby,
wherein said controller is configured to cause said at least one primary electrode to apply said first electrical signal that stimulates neural activity in the pudendal nerve to produce an increase in bladder capacity, wherein the first electrical signal comprises an AC waveform having a frequency in the range of from 1-50 Hz and wherein the first electrical signal has an amplitude in the range from 0.1 to 10 T.

Clause 2. An apparatus according to clause 1 wherein the first electrical signal has an amplitude in the range from 0.3 T to <2.0 T.

Clause 3. An apparatus according to clause 1 or clause 2 wherein the first electrical signal has an amplitude in the range from 1 T to 1.5 T.

Clause 4. An apparatus according to any one of clauses 1-3 wherein the first electrical signal comprises an AC waveform having a frequency in the range of from 1-20 Hz.

Clause 5. An apparatus according to any one of clauses 1-4 wherein the first electrical signal comprises an AC waveform having a frequency of 10 Hz or 20 Hz.

Clause 6. An apparatus according to clause 1 wherein the first electrical signal has an amplitude in the range from 2 T to 10 T.

Clause 7. An apparatus according to clause 6 wherein the first electrical signal has an amplitude in the range from 2 T to 4 T, optionally 3 T.

Clause 8. An apparatus according to clause 6 or clause 7 wherein the first electrical signal comprises an AC waveform having a frequency in the range of from 1-20 Hz.

Clause 9. An apparatus according to clause 8 wherein the first electrical signal comprises an AC waveform having a frequency of 10 Hz.

Clause 10. An apparatus according to any one of clauses 1 to 9, wherein said at least one primary electrode is configured to apply said first electrical signal to sensory fibres of said pudendal nerve, and said controller is configured to cause said at least one primary electrode to apply said first electrical signal that stimulates neural activity in sensory fibres of the pudendal nerve to produce an increase in bladder capacity.

Clause 11. An apparatus according to any one of clauses 1-10, wherein said controller is configured to cause a second electrical signal to be applied, wherein said second electrical signal stimulates neural activity in the pudendal nerve to produce an increase in voiding efficiency and wherein the second electrical signal comprises an AC waveform having a frequency higher than the frequency of the first electrical signal.

Clause 12. An apparatus according to clause 11, wherein said second electrical signal is applied by said at least one primary electrode(s).

Clause 13. An apparatus according to clause 11, wherein said second electrical signal is applied by at least one secondary electrode(s) coupled to said controller, said controller controlling the signal to be applied thereby.

Clause 14. An apparatus according to any one of clauses 1-10, further comprising at least one secondary electrode configured to apply a second electrical signal to said nerve and coupled to said controller, said controller controlling the signal to be applied thereby,
wherein said controller is configured to cause said secondary electrode to apply said second electrical signal that stimulates neural activity in the pudendal nerve to produce an increase in voiding efficiency, wherein the second electrical signal comprises an AC waveform and wherein said controller is configured to cause said second electrical signal to be applied in a burst pattern.

Clause 15. An apparatus according to clause 14, wherein said burst pattern consists of a signal burst having a duration from 50 ms to 1000 ms repeated at an interval of from 0.2 s to 2 s.

Clause 16. An apparatus according to clause 14 or 15, wherein said burst pattern consists of a signal burst having a duration of 100 ms repeated at an interval of 0.5 s.

Clause 17. An apparatus according to any one of clauses 11-16, wherein the second electrical signal comprises an AC waveform having a frequency in the range of from 20-50 Hz.

Clause 18. An apparatus according to clause 17 wherein the second electrical signal comprises an AC waveform having a frequency of 30-40 Hz, optionally 33 Hz or 40 Hz.

Clause 19. An apparatus according to any one of clauses 11-18 wherein the second electrical signal comprises an AC waveform has an amplitude in the range of 0.5-4 T, optionally 1-3 T.

Clause 20. An apparatus according to clause 14-19, wherein said at least one secondary electrode is configured to apply said second electrical signal to motor fibres of said pudendal nerve, and said controller is configured to cause said at least one secondary electrode(s) to apply said second electrical signal that stimulates neural activity in motor fibres of the pudendal nerve to produce an increase in voiding efficiency.

Clause 21. An apparatus according to any one of clauses 1 to 20, wherein said primary electrode(s) is a bipolar cuff electrode.

Clause 22. An apparatus according to any one of clauses 13-21, wherein said secondary electrode(s) is a bipolar cuff electrode.

Clause 23. An apparatus according to any one of clauses 1-22, wherein the apparatus further comprises a detector to detect one or more physiological parameters in the subject, wherein the controller is coupled to said detector, and causes the electrical signal to be applied when a physiological parameter is detected to be meeting or exceeding a predefined threshold value.

Clause 24. An apparatus according to clause 23, wherein one or more of the detected physiological parameters is selected from nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

Clause 25. An apparatus according to any one of clauses 23 or 24, wherein the controller causes the first electronic signal to be stopped when the detector detects onset of a bladder voiding phase.

Clause 26. An apparatus according to any one of clauses 1-25, wherein the controller is configured to cause the first electrical signal to be applied no more frequently than alternate micturition cycles, optionally no more frequently than every third micturition cycle.

Clause 27. An apparatus according to any one of clauses 1-26, further comprising an input element, wherein the input element allows the subject to enter data regarding their behaviour and/or desires so as to determine when the controller causes the electrical signal to be applied.

Clause 28. An apparatus according to clause 27, wherein the input element is in wireless communication with the controller.

Clause 29. An apparatus according to any one of clauses 1-28 wherein the apparatus is suitable for at least partial implantation into the subject, optionally full implantation into the subject.

Clause 30. A method of treating bladder dysfunction in a subject comprising:
  i. implanting in the subject an apparatus according to any one of clauses 1-29;
  ii. positioning at least one primary electrode of the apparatus in signalling contact with a pudendal nerve of the subject and, when the apparatus comprises at least one secondary electrode, positioning said at least one secondary electrode of the apparatus in signalling contact with a pudendal nerve of the subject;
  iii. activating the apparatus to apply an electrical signal to the pudendal nerve of the subject as caused by the controller.

Clause 31. A method of treating bladder dysfunction in a subject comprising applying a first electrical signal to a pudendal nerve of the subject, wherein the first electrical signal comprises an AC waveform having a frequency in the range of from 1-50 Hz and wherein the first electrical signal has an amplitude in the range of from 0.1 to 10 T.

Clause 32. A method according to clause 31, wherein said first electrical signal is applied to the pudendal nerve during a bladder filling phase, wherein application of said first electrical signal increases bladder capacity.

Clause 33. A method according to any one of clauses 31-32 wherein application of said first electrical signal is stopped at the onset of a bladder voiding phase.

Clause 34. A method according to any one of clauses 31-33, wherein the first electrical signal has an amplitude in the range from 0.3 T to <2.0 T.

Clause 35. A method according to clause 34 wherein the first electrical signal has an amplitude in the range from 1 T to 1.5 T.

Clause 36. A method according to any one of clauses 31-35, wherein the first electrical signal comprises an AC waveform having a frequency in the range of from 1-20 Hz.

Clause 37. A method according to clause 36 wherein the first electrical signal comprises an AC waveform having a frequency of 10 Hz or 20 Hz.

Clause 38. A method according to any one of clauses 31-33 wherein the first electrical signal has an amplitude in the range of from 2 T to 10 T.

Clause 39. A method according to clause 38 wherein the first electrical signal has an amplitude in the range from 2 T to 4 T, optionally 3 T.

Clause 40. A method according to clause 38 or clause 39 wherein the first electrical signal comprises an AC waveform having a frequency in the range of from 1-20 Hz.

Clause 41. A method according to clause 40 wherein the first electrical signal comprises an AC waveform having a frequency of 10 Hz.

Clause 42. A method according to any one of clauses 31-41, further comprising applying a second electrical signal to a pudendal nerve of the subject, wherein the second electrical signal comprises an AC waveform having a frequency higher than the frequency of the first electrical signal.

Clause 43. A method according to any one of clauses 31-41, further comprising applying a second electrical signal to a pudendal nerve of the subject, wherein the second electrical signal comprises an AC waveform and is applied in a burst pattern.

Clause 44. A method according to clause 43, wherein said burst pattern consists of a signal burst having a duration from 50 ms to 1000 ms repeated at an interval of from 0.125 s to 2 s.

Clause 45. A method according to clause 44, wherein said burst pattern consists of a signal burst having a duration of 100 ms repeated at an interval of 0.5 s.

Clause 46. A method according to any one of clauses 42-45, wherein said second electrical signal is applied to the pudendal nerve during a bladder voiding phase, wherein application of said second electrical signal promotes bladder voiding.

Clause 47. A method according to any one of clauses 42-46, wherein the second electrical signal comprises an AC waveform having a frequency in the range of from 20-50 Hz.

Clause 48. A method according to clause 47 wherein the second electrical signal comprises an AC waveform having a frequency of 30-40 Hz, optionally 33 Hz or 40 Hz.

Clause 49. A method according to any one of clauses 42-48 wherein the second electrical signal comprises an AC waveform has an amplitude in the range from 0.5-4 T, optionally from 1-3 T.

Clause 50. A method according to any one of clauses 43-49, wherein the second electrical signal is applied to motor fibres of the pudendal nerve.

Clause 51. A method according to any one of clauses 30-50, wherein the first electronic signal is applied bilaterally and, in a method according to clause 31, the apparatus comprises two primary electrodes and step (ii) comprises positioning the primary electrodes bilaterally.

Clause 52. A method according to any one of clauses 30, and 42-51, wherein the second electronic signal is applied bilaterally and, in a method according to clause 30, the apparatus comprises two secondary electrodes and step (ii) comprises positioning the secondary electrodes bilaterally.

Clause 53. A method according to any one of clauses 31-52, wherein the first electronic signal is applied no more frequently than alternate micturition cycles, optionally no more frequently than every third micturition cycle.

Clause 54. A pharmaceutical composition comprising a compound for treating bladder dysfunction, for use in a method of treating bladder dysfunction in a subject, wherein the method is a method according to any one of clauses 30-53, the method further comprising the step of administering an effective amount of the pharmaceutical composition to the subject.

Clause 55. A pharmaceutical composition comprising a compound for treating bladder dysfunction, for use in treating bladder dysfunction in a subject, the subject having an apparatus according to any one of clauses 1-29 implanted.

Clause 56. A pharmaceutical composition for use according to clause 54 or 55, wherein the compound for treating bladder dysfunction is an antimuscarinic compound or a β-adrenergic receptor agonist, optionally a β3-adrenergic receptor agonist.

Clause 57. A pharmaceutical composition for use according to any one of clauses 54-56, wherein the compound for treating bladder dysfunction is an antimuscarinic compound selected from darifenacin, hyoscyamine, oxybutynin, tolterodine, solifenacin, trospium, or fesoterodine.

Clause 58. A pharmaceutical composition for use according to any one of clauses 54-56, wherein the compound for treating bladder dysfunction is a β3-adrenergic receptor agonist, optionally mirabegron.

Clause 59. A neuromodulation system comprising a plurality of apparatuses according to any one of clauses 1-29.

Clause 60. A neuromodulation system according to clause 59, wherein each apparatus is arranged to communicate with at least one other apparatus in the system, optionally all apparatuses in the system.

Clause 61. A neuromodulation system according to clause 59 or 60, further comprising a processor arranged to communicate with the apparatuses of the system.

The invention claimed is:

1. An apparatus for stimulating neural activity in a pudendal nerve of a subject, the apparatus comprising: at least one primary electrode configured to apply a first electrical signal to said nerve; and a controller coupled to said primary electrode(s) and controlling the first electrical signal to be applied thereby, wherein said controller is configured to cause said at least one primary electrode to apply said first electrical signal that stimulates neural activity in the pudendal nerve to produce an increase in bladder capacity, wherein the first electrical signal comprises an AC waveform having a frequency in the range of from 0.1-50 Hz, wherein the first electrical signal has an amplitude in the range from 0.05 T to 10 T, wherein T is the threshold stimulation intensity required to evoke a reflex EMG response in the EUS of the subject, and wherein application of the first electrical signal is stopped at onset of a bladder voiding phase, resulting in improved voiding efficiency.

2. The apparatus according to claim 1 in which the first electrical signal is applied no more frequently than alternate micturition cycles.

3. The apparatus according to claim 1, in which at least the first electrical signal is applied to sensory fibres of the pudendal nerve.

4. The apparatus according to claim 3 in which the signal is applied to a sensory branch of the pudendal nerve.

5. The apparatus according to claim 4 in which the at least one primary electrode is configured to apply the first electrical signal to the sensory branch of the pudendal nerve, and the controller is configured to cause said at least one primary electrode to apply the first electrical signal that stimulates neural activity in the sensory branch of the pudendal nerve to produce an increase in bladder capacity.

6. The apparatus according to claim 1 in which the controller causes the first electrical signal to be stopped when onset of a voiding phase is detected.

7. The apparatus according to claim 1 wherein said controller is configured to cause a second signal to be applied wherein said second signal stimulates the pudendal nerve, wherein said second electrical signal stimulates neural activity in the pudendal nerve to produce an increase in voiding efficiency and wherein the second electrical signal comprises an AC waveform having a frequency in the range of from 20 to 50 Hz.

8. The apparatus according to claim 7 wherein the second electrical signal is applied by said at least one primary electrode(s) or wherein the apparatus comprises at least one secondary electrode coupled to the controller and the second electrical signal is applied by the at least one secondary electrode(s), the controller controlling the signal to be applied thereby.

9. The apparatus according to claim 7 in which the second electrical signal is applied in a burst pattern comprising a signal burst comprising an AC waveform, wherein the signal burst is repeated at a frequency in the range of from 0.5-20 Hz.

10. The apparatus according to claim 9 in which the burst pattern comprises a signal burst having a duration from 50 ms to 1000 ms repeated at an interval of from 0.125 s to 2 s.

11. The apparatus according to claim 7 in which the second electrical signal is to be applied to motor fibres of the pudendal nerve.

12. The apparatus according to claim 11 in which the at least one secondary electrode(s) is (are) configured to apply the second electrical signal to motor fibres of said pudendal nerve, and the controller is configured to cause said at least one secondary electrode to apply the second electrical signal that stimulates neural activity in motor fibres of the pudendal nerve to produce an increase in voiding efficiency.

13. The apparatus according to claim 7 in which a second electrical signal is (to be) applied, the second electrical signal comprises an AC waveform having an amplitude in the range of 0.5-4 T.

14. A method of treating bladder dysfunction in a subject comprising applying a first electrical signal to a pudendal nerve of the subject, wherein the first electrical signal comprises an AC waveform having a frequency in the range of from 1-50 Hz, wherein the first electrical signal has an amplitude in the range of from 0.05 T to 10 T, wherein T is the threshold stimulation intensity required to evoke a reflex EMG response in the EUS of the subject, and wherein application of the first electrical signal is stopped at onset of a bladder voiding phase, resulting in improved voiding efficiency.

15. The method according to claim 14 in which the first electrical signal is applied no more frequently than alternate micturition cycles.

16. The method according to claim 14 in which the first electrical signal is applied to sensory fibres of the pudendal nerve.

17. The method according to claim 16 in which the signal is applied to a sensory branch of the pudendal nerve.

18. The method according to claim 14 further comprising the application of a second electrical signal to stimulate the pudendal nerve.

19. The method according to claim 18 in which the second electrical signal applied comprises an AC waveform having a frequency in the range from 20-50 Hz.

20. The method according to claim 18 in which the second electrical signal comprises an AC waveform and is applied in a burst pattern.

21. The method according to claim 20 in which the burst pattern comprises a signal burst having a duration from 50 ms to 1000 ms.

22. The method according to claim 18 in which the second electrical signal is to be applied to motor fibres of the pudendal nerve.

23. The method according to claim 20 in which the second electrical signal applied in a burst pattern comprises an AC waveform having a frequency in the range of from 20-50 Hz.

24. The method according to claim 20 in which the second electrical signal is applied in a burst pattern comprising a signal burst comprising the AC waveform, wherein the signal burst is repeated at a frequency in the range of from 2 to 20 Hz.

25. The method according to claim 20 wherein the burst pattern is repeated at an interval of from 0.125 s to 2 s.

26. The method according to claim 20 in which a second electrical signal is (to be) applied, wherein the second electrical signal comprises an AC waveform having an amplitude in the range of 0.5-4 T.

\* \* \* \* \*